(12) United States Patent
Jain et al.

(10) Patent No.: US 10,155,975 B2
(45) Date of Patent: Dec. 18, 2018

(54) POLYMERASE CHAIN REACTION DETECTION SYSTEM

(71) Applicant: LGC Genomics Ltd, Teddington (GB)

(72) Inventors: Nisha Jain, Hoddesdon (GB); John Edmond Holme, Hoddesdon (GB)

(73) Assignee: LGC Genomics Ltd (GB)

( * ) Notice: Subject to any disclaimer, the term of this patent is extended or adjusted under 35 U.S.C. 154(b) by 289 days.

(21) Appl. No.: 14/769,792

(22) PCT Filed: Mar. 5, 2014

(86) PCT No.: PCT/GB2014/050650
§ 371 (c)(1),
(2) Date: Aug. 21, 2015

(87) PCT Pub. No.: WO2014/135872
PCT Pub. Date: Sep. 12, 2014

(65) Prior Publication Data
US 2016/0002712 A1    Jan. 7, 2016

(30) Foreign Application Priority Data
Mar. 6, 2013   (GB) .................................. 1304030.8

(51) Int. Cl.
*C12P 19/34*   (2006.01)
*C12Q 1/6818*  (2018.01)
*C12Q 1/6858*  (2018.01)

(52) U.S. Cl.
CPC ......... *C12Q 1/6818* (2013.01); *C12Q 1/6858* (2013.01)

(58) Field of Classification Search
CPC ............ C12Q 1/6858; C12Q 2527/107; C12Q 2565/101; C12Q 1/6818
USPC ....................................................... 435/91.2
See application file for complete search history.

(56) References Cited

U.S. PATENT DOCUMENTS

| | | | |
|---|---|---|---|
| 2007/0015180 A1* | 1/2007 | Sorge ..................... | C07H 21/04 435/6.11 |
| 2010/0105050 A1* | 4/2010 | Hodge ................... | C12Q 1/682 435/6.14 |
| 2011/0136116 A1* | 6/2011 | Barany ................. | C12Q 1/6827 435/6.11 |

FOREIGN PATENT DOCUMENTS

| | | |
|---|---|---|
| EP | 0744470 A1 | 11/1996 |
| EP | 1 666 609 A1 | 6/2006 |
| EP | 1 726 664 A1 | 11/2006 |
| WO | 99/49293 A2 | 9/1999 |
| WO | 2006/119326 A2 | 11/2006 |
| WO | WO2012/154876 A1 | 11/2012 |
| WO | 2013/140107 A1 | 9/2013 |

OTHER PUBLICATIONS

Barnes, W. (1994). PCR amplification of up to 35-kb DNA with high fidelity and high yield from lambda bacteriophage templates. Proc. Natl. Acad. Sci USA; 91: 2216-2220.

Braithwaite, D and Ito, J. (1993). Compilation, alignment, and phylogenetic relationships of DNA polymerases. Nucleic Acids Res; 21: 787-802.

De Noronha C and Mullins J. (1992) Amplimers with 3'-terminal phosphorothioate linkages resist degradation by vent polymerase and reduce Taq polymerase mispriming. PCR Methods & Applications, Cold Spring Harbor Laboratory Press; 2(2): 131-136.

Lebedev, A, et al. (2008). 'Hot Start PCR with heat-activatable primers: a novel approach for improved PCR performance' Nucleic Acids Res; 36(20): E131.

Moretti, T, et al. (1998) Enhancement of PCR amplification yield and specificity using AmpliTaq Gold DNA polymerase. Biotechniques; 25: 716-722.

\* cited by examiner

*Primary Examiner* — Cynthia B Wilder
(74) *Attorney, Agent, or Firm* — Geoffrey M. Karny

(57) ABSTRACT

The present invention relates to methods and kits for nucleic acid detection in an assay system.

16 Claims, 17 Drawing Sheets

Specification includes a Sequence Listing.

SNP ———[A/G]———

There are two
possible outcomes ———A———
Parrallele for this SNP  or
———G———

The primers involves in this reaction are as follows:

Allele specific primer 1          Respective Fluor/Quencher

FAM

Allele specific Primer 2          Respective Fluor/Quencher

HEX

Common Primer    5'———————3'

SNP ———[A/G/T/C]———

There are four
possible outcomes      ———A———            ———T———
per Allele for this SNP    or                or
                       ———G———            ———C———

The primers involves in this reaction are as follows:

Allele specific primer 1        Respective Fluor/Quencher
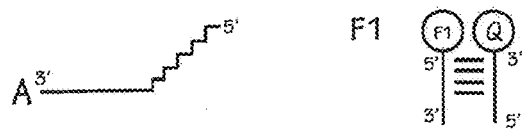

Allele specific Primer 2        Respective Fluor/Quencher
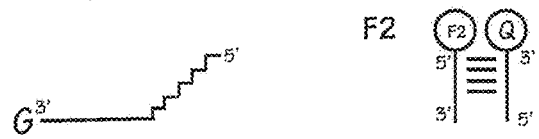

Common Primer 1  5'———————3'

Allele specific primer 3        Respective Fluor/Quencher
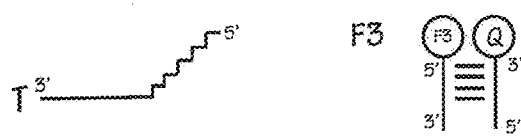

Allele specific Primer 4        Respective Fluor/Quencher
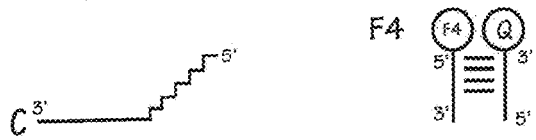

Common Primer 2  5'———————3'

*FIG. 5A*

SNP 1 ——[A/G]—— SNP 2 ——[A/G]——

There are two possible outcomes Per Allele for this SNP: ——A—— or ——G——

There are two possible outcomes Per Allele for this SNP: ——A—— or ——G——

The primers involves in this reaction are as follows:

Allele specific primer 1

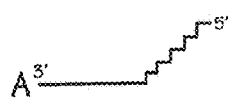

Respective Fluor/Quencher

F1 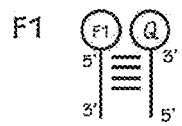

Allele specific Primer 2

Respective Fluor/Quencher

F2 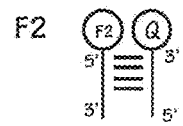

Common Primer 1   5'————————3'

Allele specific primer 3

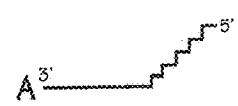

Respective Fluor/Quencher

F3 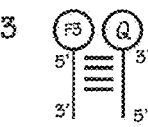

Allele specific Primer 4

Respective Fluor/Quencher

F4 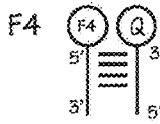

Common Primer 2   5'————————3'

FIG. 5B

SEQUENCE LISTING

<160> NUMBER OF SEQ ID NOS: 26

<210> SEQ ID NO 1
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /mol_type="unassigned DNA"
      /note="Cassette Pair 1 FAM fluorescent oligonucleotide"
      /organism="Artificial Sequence"

<400> SEQUENCE: 1
tgagcgatta gccgttagga tga                                          23

<210> SEQ ID NO 2
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
    /note="Cassette Pair 1 FAM complementary quenching
    oligonucleotide"
    /organism="Artificial Sequence"

<400> SEQUENCE: 2
aacctaacgg ctaatcgctc a                                           21

<210> SEQ ID NO 3
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /mol_type="unassigned DNA"
    /note="Cassette Pair 1 HEX fluorescent oligonucleotide"
    /organism="Artificial Sequence"

<400> SEQUENCE: 3
gctggtcggt gaacaggtta gaga                                        24

<210> SEQ ID NO 4
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
    /note="Cassette Pair 1 HEX complementary quenching
    oligonucleotide"
    /organism="Artificial Sequence"

<400> SEQUENCE: 4
taacctgttc accgaccagc                                             20

<210> SEQ ID NO 5
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="unassigned DNA"
    /note="Cassette Pair 2 FAM fluorescent oligonucleotide"
    /organism="Artificial Sequence"

<400> SEQUENCE: 5
tcagtgagcg attagccgtt aggatga                                     27

<210> SEQ ID NO 6
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
    /note="Cassette Pair 2 FAM complementary quenching
    oligonucleotide"
    /organism="Artificial Sequence"

```
<400> SEQUENCE: 6
aacctaacgg ctaatcgctc actga                                          25

<210> SEQ ID NO 7
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="Cassette Pair 2 HEX fluorescent oligonucleotide"
      /organism="Artificial Sequence"

<400> SEQUENCE: 7
tacagctggt cggtgaacag gttagaga                                       28

<210> SEQ ID NO 8
<211> LENGTH: 24
<212> TYPE: DNA
<213> ORGANISM: Artificial Sequence
<220> FEATURE:
<221> NAME/KEY: source
<222> LOCATION: 1..24
<223> OTHER INFORMATION: /mol_type="unassigned DNA"
      /note="Cassette Pair 2 HEX complementary quenching
      oligonucleotide"
      /organism="Artificial Sequence"

<400> SEQUENCE: 8
taacctgttc accgaccagc tgta                                           24

<210> SEQ ID NO 9
<211> LENGTH: 31
<212> TYPE: DNA
<213> ORGANISM: Artificial Sequence
<220> FEATURE:
<221> NAME/KEY: source
<222> LOCATION: 1..31
<223> OTHER INFORMATION: /mol_type="unassigned DNA"
      /note="Cassette Pair 3 FAM fluorescent oligonucleotide"
      /organism="Artificial Sequence"

<400> SEQUENCE: 9
tgtctcagtg agcgattagc cgttaggatg a                                   31

<210> SEQ ID NO 10
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="Cassette Pair 3 FAM complementary quenching
      oligonucleotide"
      /organism="Artificial Sequence"

<400> SEQUENCE: 10
aacctaacgg ctaatcgctc actgagaca                                      29

<210> SEQ ID NO 11
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="unassigned DNA"
```

```
              /note="Cassette Pair 3 HEX fluorescent oligonucleotide"
              /organism="Artificial Sequence"

<400> SEQUENCE: 11
atgctacagc tggtcggtga acaggttaga ga                                    32

<210> SEQ ID NO 12
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="unassigned DNA"
      /note="Cassette Pair 3 HEX complementary quenching
      oligonucleotide"
      /organism="Artificial Sequence"

<400> SEQUENCE: 12
taacctgttc accgaccagc tgtagca                                          27

<210> SEQ ID NO 13
<211> LENGTH: 35
<212> TYPE: DNA
<213> ORGANISM: Artificial Sequence
<220> FEATURE:
<221> NAME/KEY: source
<222> LOCATION: 1..35
<223> OTHER INFORMATION: /mol_type="unassigned DNA"
      /note="Cassette Pair 4 FAM fluorescent oligonucleotide"
      /organism="Artificial Sequence"

<400> SEQUENCE: 13
atgctgtctc agtgagcgat tagccgttag gatga                                 35

<210> SEQ ID NO 14
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="unassigned DNA"
      /note="Cassette Pair 4 FAM complementary quenching
      oligonucleotide"
      /organism="Artificial Sequence"

<400> SEQUENCE: 14
aacctaacgg ctaatcgctc actgagacag cat                                   33

<210> SEQ ID NO 15
<211> LENGTH: 36
<212> TYPE: DNA
<213> ORGANISM: Artificial Sequence
<220> FEATURE:
<221> NAME/KEY: source
<222> LOCATION: 1..36
<223> OTHER INFORMATION: /mol_type="unassigned DNA"
      /note="Cassette Pair 4 HEX fluorescent oligonucleotide"
      /organism="Artificial Sequence"

<400> SEQUENCE: 15
aagcatgcta cagctggtcg gtgaacaggt tagaga                                36

<210> SEQ ID NO 16
<211> LENGTH: 32
<212> TYPE: DNA
<213> ORGANISM: Artificial Sequence
<220> FEATURE:
```

```
<221> NAME/KEY: source
<222> LOCATION: 1..32
<223> OTHER INFORMATION: /mol_type="unassigned DNA"
      /note="Cassette Pair 4 HEX complementary quenching
      oligonucleotide"
      /organism="Artificial Sequence"

<400> SEQUENCE: 16
taacctgttc accgaccagc tgtagcatgc tt                                  32

<210> SEQ ID NO 17
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Cassette Pair 5 FAM fluorescent oligonucleotide"
      /organism="Artificial Sequence"

<400> SEQUENCE: 17
gcgattagcc gttaggatga                                                20

<210> SEQ ID NO 18
<211> LENGTH: 16
<212> TYPE: DNA
<213> ORGANISM: Artificial Sequence
<220> FEATURE:
<221> NAME/KEY: source
<222> LOCATION: 1..16
<223> OTHER INFORMATION: /mol_type="unassigned DNA"
      /note="Cassette Pair 5 FAM complementary quenching
      oligonucleotide"
      /organism="Artificial Sequence"

<400> SEQUENCE: 18
cctaacggct aatcgc                                                    16

<210> SEQ ID NO 19
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Cassette Pair 5 HEX fluorescent oligonucleotide"
      /organism="Artificial Sequence"

<400> SEQUENCE: 19
gtcggtgaac aggttagaga                                                20

<210> SEQ ID NO 20
<211> LENGTH: 15
<212> TYPE: DNA
<213> ORGANISM: Artificial Sequence
<220> FEATURE:
<221> NAME/KEY: source
<222> LOCATION: 1..15
<223> OTHER INFORMATION: /mol_type="unassigned DNA"
      /note="Cassette Pair 5 HEX complementary quenching
      oligonucleotide"
      /organism="Artificial Sequence"

<400> SEQUENCE: 20
aacctgttca ccgac                                                     15

<210> SEQ ID NO 21
```

```
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Primer"
      /organism="Artificial Sequence"

<400> SEQUENCE: 21
gcgattagcc gttaggatga tgaagctcca caatttggtg aattatcaat           50

<210> SEQ ID NO 22
<211> LENGTH: 50
<212> TYPE: DNA
<213> ORGANISM: Artificial Sequence
<220> FEATURE:
<221> NAME/KEY: source
<222> LOCATION: 1..50
<223> OTHER INFORMATION: /mol_type="unassigned DNA"
      /note="Primer"
      /organism="Artificial Sequence"

<400> SEQUENCE: 22
gtcggtgaac aggttagaga tgaagctcca caatttggtg aattatcaaa           50

<210> SEQ ID NO 23
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="Primer"
      /organism="Artificial Sequence"

<400> SEQUENCE: 23
cactctagta ctatatctgt cacatggta                                  29

<210> SEQ ID NO 24
<211> LENGTH: 43
<212> TYPE: DNA
<213> ORGANISM: Artificial Sequence
<220> FEATURE:
<221> NAME/KEY: source
<222> LOCATION: 1..43
<223> OTHER INFORMATION: /mol_type="unassigned DNA"
      /note="Primer"
      /organism="Artificial Sequence"

<400> SEQUENCE: 24
gcgattagcc gttaggatga tcattctcat aatcgcccac gga                  43

<210> SEQ ID NO 25
<211> LENGTH: 43
<212> TYPE: DNA
<213> ORGANISM: Artificial Sequence
<220> FEATURE:
<221> NAME/KEY: source
<222> LOCATION: 1..43
<223> OTHER INFORMATION: /mol_type="unassigned DNA"
      /note="Primer"
      /organism="Artificial Sequence"

<400> SEQUENCE: 25
gtcggtgaac aggttagaga tcattctcat aatcgcccac ggg                  43
```

```
<210> SEQ ID NO 26
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="Primer"
      /organism="Artificial Sequence"

<400> SEQUENCE: 26
gtagtttgag tttgctaggc agaatagta                                  29
```

POLYMERASE CHAIN REACTION DETECTION SYSTEM

INTRODUCTION

The present invention relates to methods and kits for nucleic acid detection in an assay system.

BACKGROUND OF THE INVENTION

The polymerase chain reaction (PCR) is a powerful method for the rapid amplification of target nucleic acid sequences. PCR has facilitated the development of gene characterisation, including gene expression and/or regulation, and molecular cloning technologies including the direct sequencing of PCR amplified DNA, the determination of allelic variation, and the detection of infectious and genetic disease disorders. PCR is performed by repeated cycles of heat denaturation of a DNA template containing the target sequence, annealing of opposing primers to the complementary DNA strands, and extension of the annealed primers with a DNA polymerase. Multiple PCR cycles result in the amplification of the nucleotide sequence delineated by the flanking amplification primers. The incorporation of a thermostable DNA polymerase into the PCR protocol obviates the need for repeated enzyme additions and permits elevated annealing and primer extension temperatures which enhance the specificity of primer:template associations. Thermostable polymerases, such as Taq DNA polymerase, thus serve to increase the specificity and simplicity of PCR.

In many PCR based amplifications, a signal producing system is employed, e.g. to detect the production of amplified product. One type of signal producing system that is used in PCR based reactions is the fluorescence resonance energy transfer (FRET) system, in which a nucleic acid detector includes fluorescence donor and acceptor groups. FRET label systems include a number of advantages over other labelling systems, including the ability to perform homogeneous assays in which a separation step of bound vs. unbound labelled nucleic acid detector is not required. A primary problem with many prior art techniques is linked to the synthesis of dual labelled fluorescent oligonucleotides. European Patent Application EP1726664 discloses a detection system which overcomes this problem by using single-labelled oligonucleotide sequences of differing melting temperature (Tm) that hybridise to one another in free solution to form a fluorescent quenched pair (fluor/quencher cassette), that upon introduction of a complementary sequence to one of the sequences generates a measurable signal, one of the sequences being of a Tm that is below the annealing temperature (Ta) of the PCR process. In this system one of the single-labelled oligonucleotide sequences is preferably more than 10 bases longer than the other and more preferably at least 15 bases longer.

In detection systems using a labelled nucleic acid detector, high fidelity amplification is critical. Due to the nature of the PCR process and Taq DNA polymerase such methods can suffer from alternative side-reactions to the desired polymerisation reaction. For example, PCR can suffer from non-specific amplification when the reaction is assembled at ambient temperature. Taq polymerase retains a fraction of its activity at all temperatures and can therefore extend primers that are not complementarily annealed, leading to the formation of undesired products. The newly-synthesised region then acts as a template for further primer extension and synthesis of undesired amplification products. However, if the reaction is heated to temperatures of around 50° C. or above before polymerisation begins, the stringency of primer annealing is increased, and synthesis of undesired PCR products is avoided or reduced.

Primer-dimer is also a common side-reaction affecting PCR. Accumulation of primer-dimer occurs because of the hybridisation and extension of the primers to each other. Formation of primer-dimer results in the depletion of the reagents and hence overall reduction of PCR efficiency and/or the production of false positive results.

Hot-start PCR is a method to reduce non-specific amplification and hence limit the formation of non-specific PCR products including primer-dimers. Many different approaches have been developed to achieve this; see, for example, Moretti, T. et al. Enhancement of PCR amplification yield and specificity using AmpliTaq Gold DNA polymerase. *Bio Techniques* 25, 716-22 (1998) and Hot Start PCR with heat-activatable primers: a novel approach for improved PCR performance *Nucleic Acids Res* (2008) 36(20): e131. Such methods reduce the extension of primers following non-specific hybridisation prior to the start of PCR. However, such techniques only achieve partial alleviation of such problems since mis-priming events including primer-dimer formation can occur, although to a lesser extent, during PCR amplification. The use of PCR probes to detect the presence of a sequence internal to the PCR primers helps prevent the detection of any such non-specific products but adds significant cost to the process since a dedicated probe is required for each individual sequence to be detected. Cost effective high throughput genetic analysis requires the use of a universal detection system but in principle this can be impacted by the detection of non-specific amplification products.

There is a need for easy-to-synthesise, low cost and reliable, specific detection systems for use in the detection of primer extension products, e.g. in homogeneous PCR assays, which address the problems encountered with existing detection systems for PCR. The term homogeneous PCR assay is well known in the art, and is one where it is not necessary physically to separate the reaction components away from each other in order to derive the result of the reaction. The present invention is based on the finding that selection of the relative lengths of labelled oligonucleotide sequences that hybridise to one another to form a fluorescent quenched pair results in improvements in nucleic acid detection assay systems, particularly when used in a real-time setting. In the invention, the Tm of the fluor/quencher cassette is designed to be above the Ta of the amplification such that any unincorporated fluorescent oligonucleotide is hybridised to the quencher oligonucleotide at the fluorescence acquisition temperature allowing the reaction to be monitored in real-time or at end point. By adjusting the length and Tm of the quencher oligonucleotide it would be expected that the increased stability of the fluor/quencher cassette would simply inhibit PCR. However it is unexpectedly found that the specificity of amplification from the fluorescent primer is improved as shown by significant increases in the difference in Cq values (also known as Ct values) between samples and no template controls in real-time, or reduced detection of no template controls in end point applications.

SUMMARY OF THE INVENTION

According to the invention there is provided a method for the detection of a primer extension product, the method comprising the steps of:

a) providing one or more oligonucleotide primer groups, each group comprising one or more oligonucleotide primer sets, each set characterised by
i) a first oligonucleotide primer (forward primer) having a target-specific portion and a 5' upstream fluorescence cassette-specific portion, and
ii) a second oligonucleotide primer (reverse primer) having a target specific portion
wherein the oligonucleotide primers in a particular set are suitable respectively for hybridisation on complementary strands of a corresponding target nucleotide sequence to permit formation of a primer extension product, for example a PCR product
and wherein the first oligonucleotide primer of each set in the same group contains a fluorescence cassette-specific portion that is capable of hybridising to the complement of the fluorescence cassette-specific portion of the first oligonucleotide primer of any set in the same group
b) providing one or more cassette oligonucleotide sets, each set characterised by
i) a first cassette oligonucleotide labelled with a fluorescent moiety (donor moiety) and having a sequence that is capable of hybridisation to the complement of the fluorescence cassette-specific portion of the first oligonucleotide primer of any set in a given oligonucleotide primer group; and
ii) a second cassette oligonucleotide labelled with an acceptor moiety (for example a quencher moiety)
wherein each set of cassette oligonucleotides hybridises to one another to form a fluorescent quenched pair, wherein the fluorescent quenched pair has a Tm A,
c) initiating the primer extension reaction thereby generating (if the relevant target polynucleotide is present) a complementary sequence to the relevant first oligonucleotide primer,
such that the relevant second (acceptor, for example quencher, labelled) cassette oligonucleotide is less able to hybridise to the relevant first (fluorescently labelled) cassette oligonucleotide, whereby a signal is generated; and
d) detecting the signal that is generated,
wherein the primer extension reaction is performed at least in part at a Ta that is less than the Tm A or Tm As for the one or more fluorescent quenched pairs.

Kits suitable for use in such a method are also provided.

BRIEF DESCRIPTION OF THE DRAWINGS

FIG. 5A-FIG. 5B shows schematic examples of possible oligonucleotide combinations for use in the present invention. The reverse primers shown for analysing multiple alleles of a gene can be common, but do not have to be.

DETAILED DESCRIPTION OF THE INVENTION

Figure 1A:
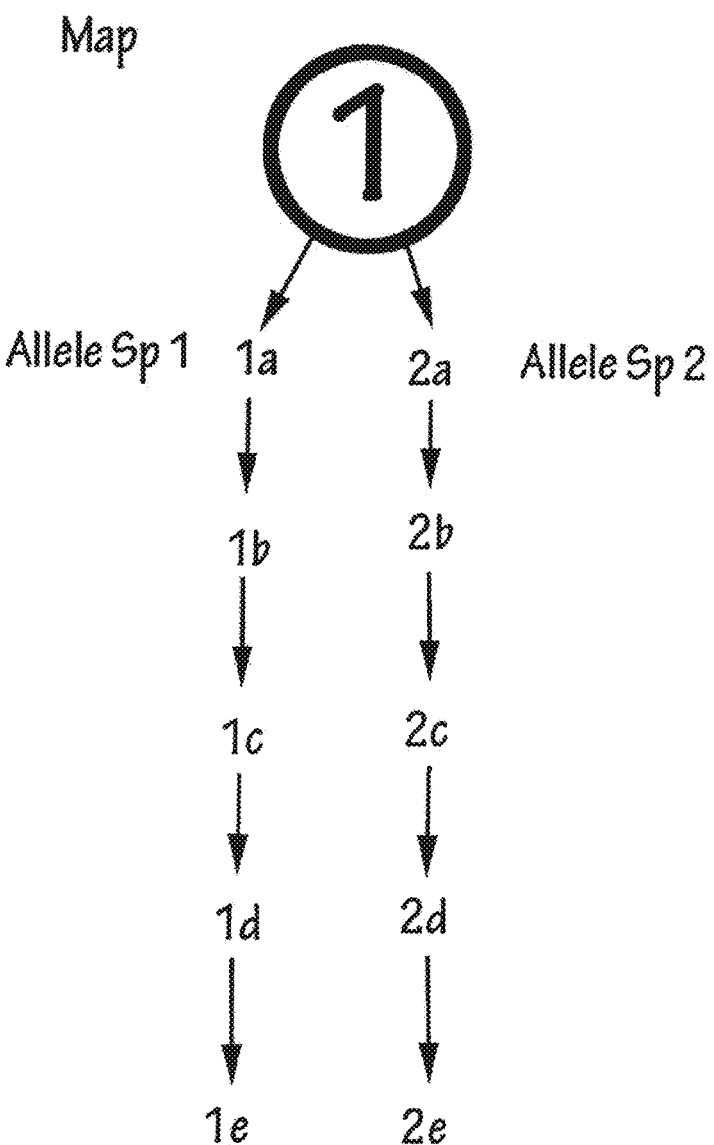
FIG. 1A-FIG. 1L is a simple reaction schema for detection of a DNA sequence in SNP Genotyping embodying a method of the present invention.
Figure 1B:
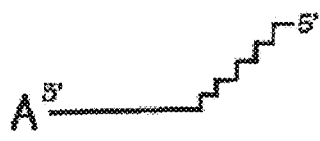
Figure 1B:
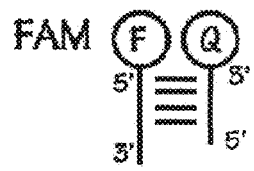
Figure 1B:
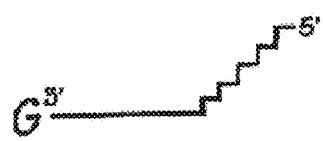
Figure 1B:
Figure 1C:
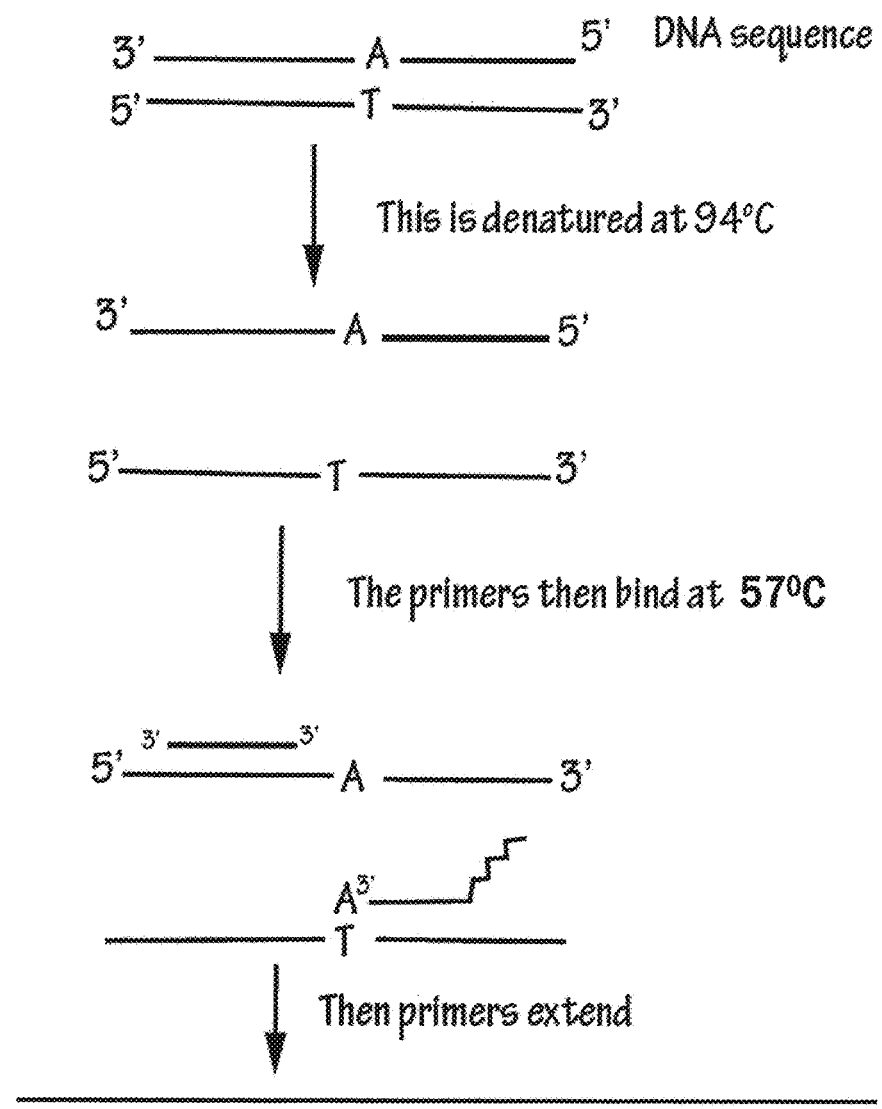
Figure 1D:
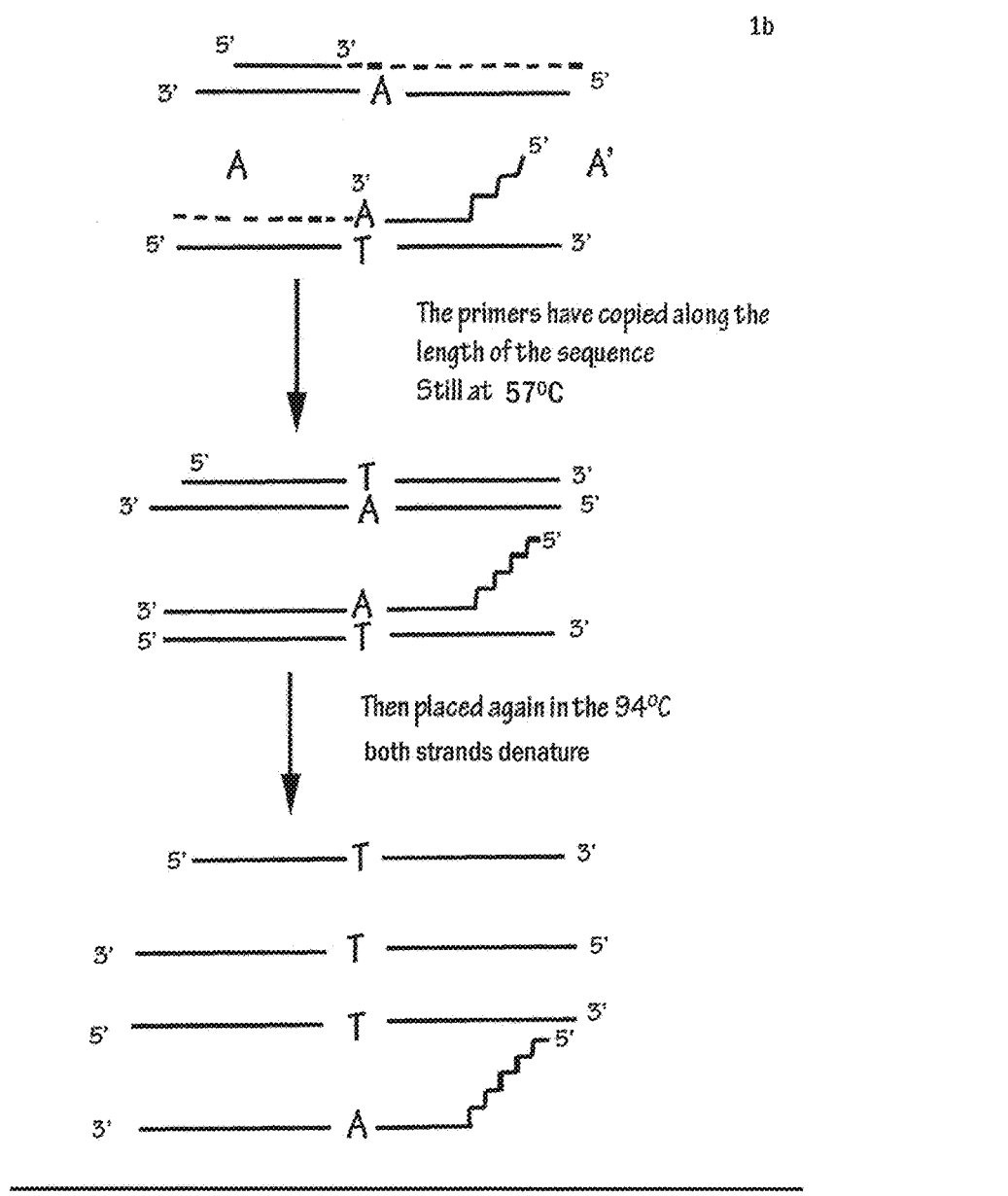
Figure 1E:
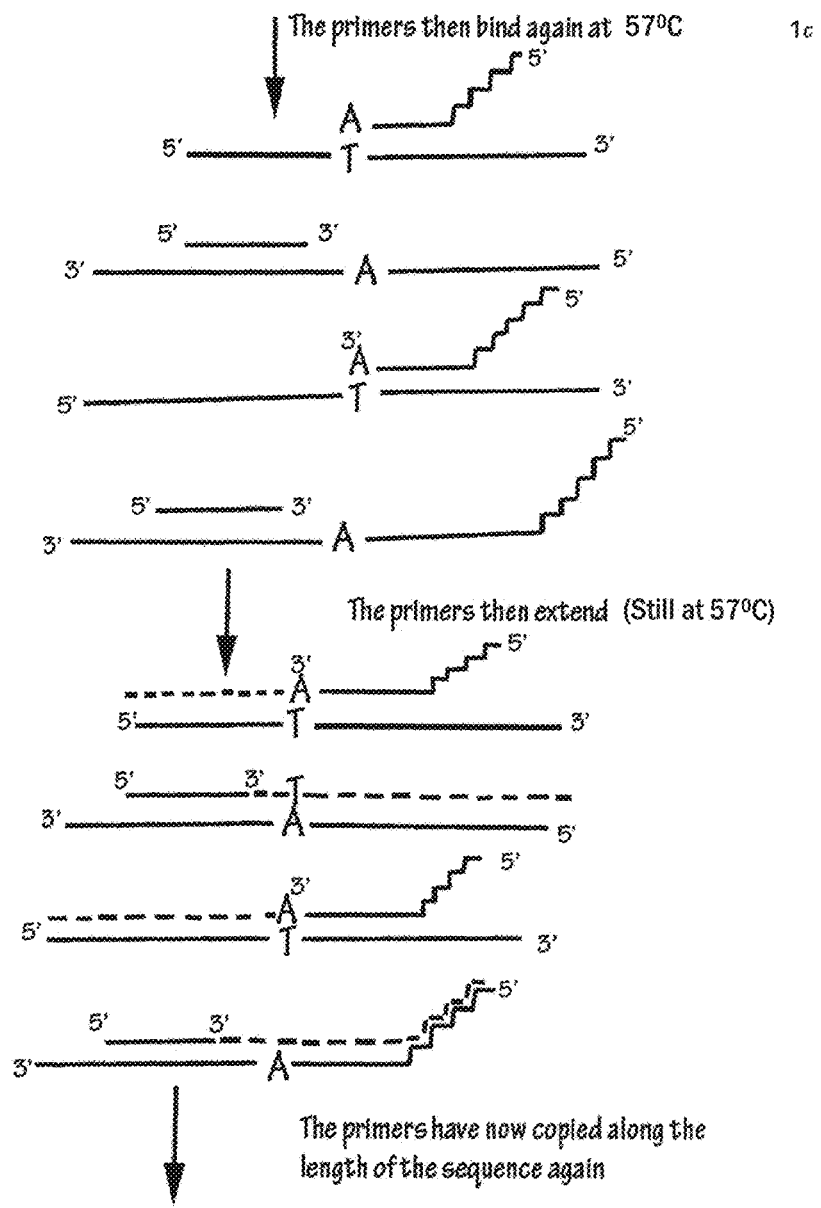
Figure 1F:
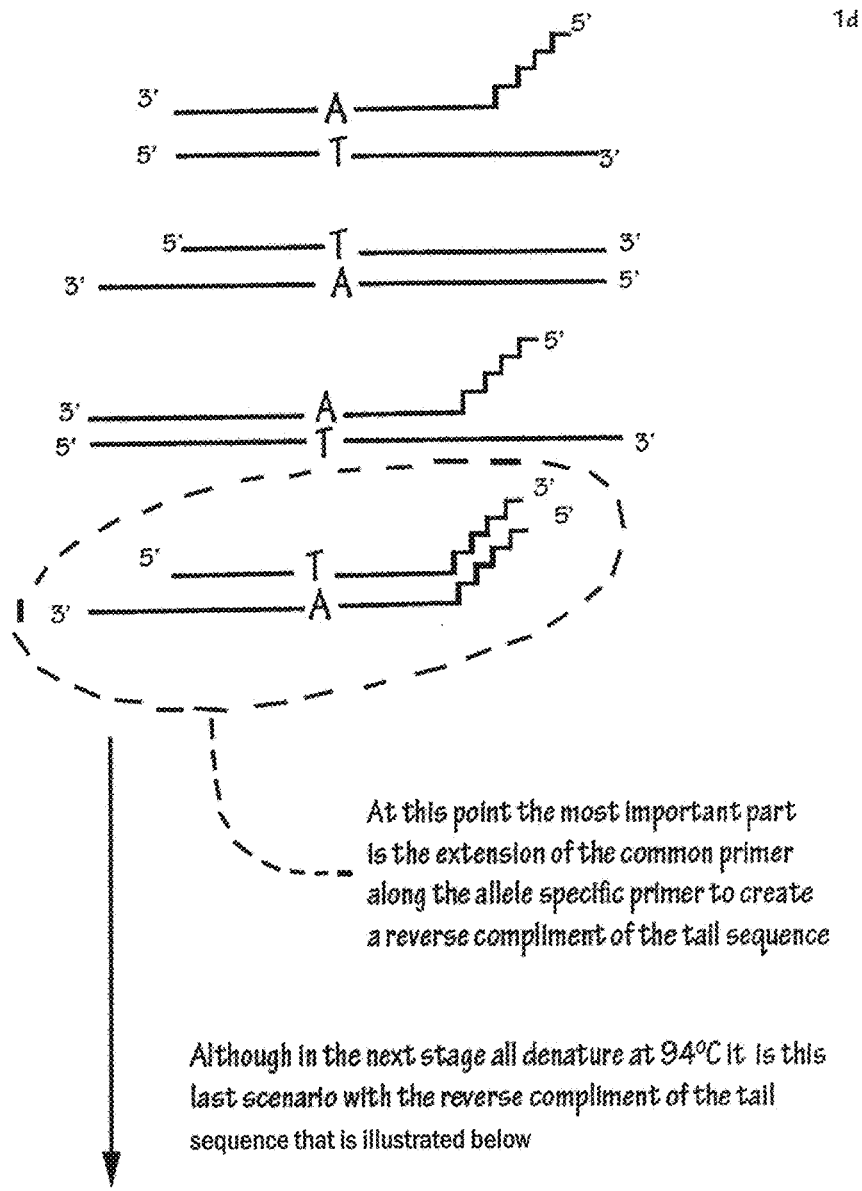
Figure 1G:
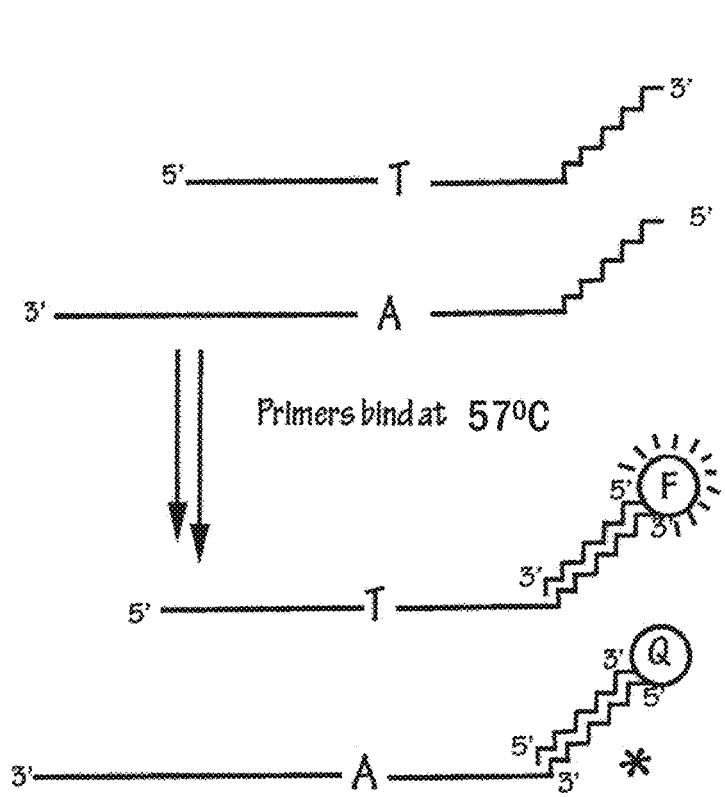
Figure 1H:
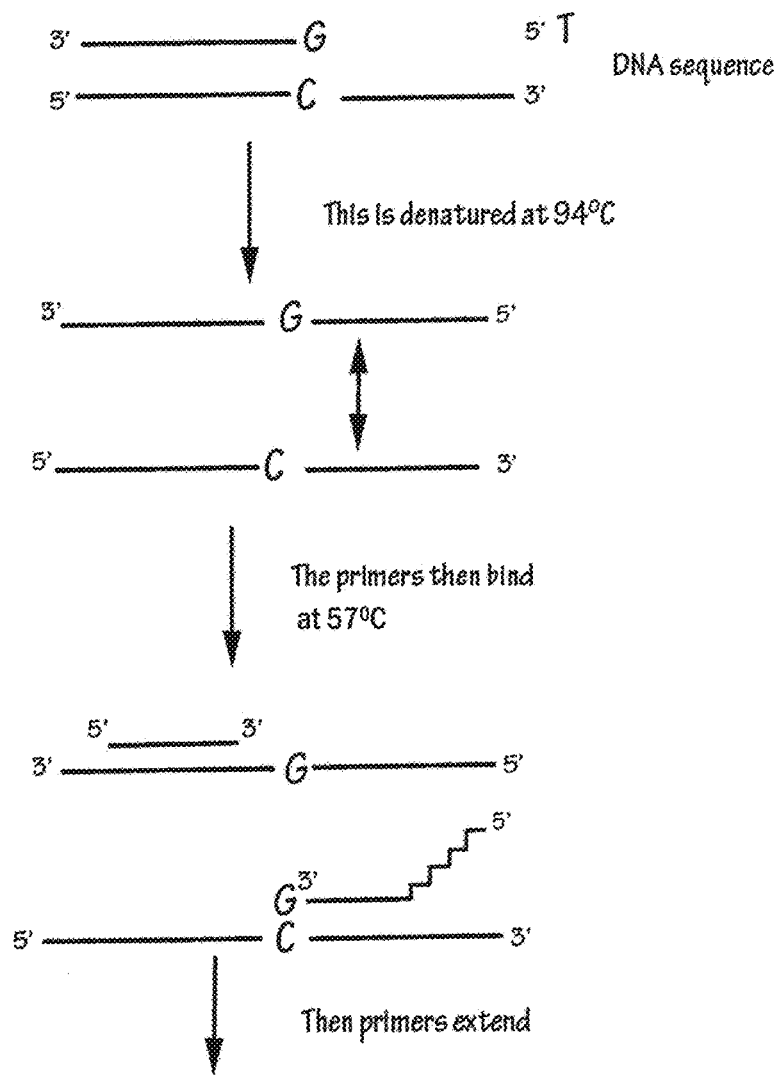
Figure 1I:
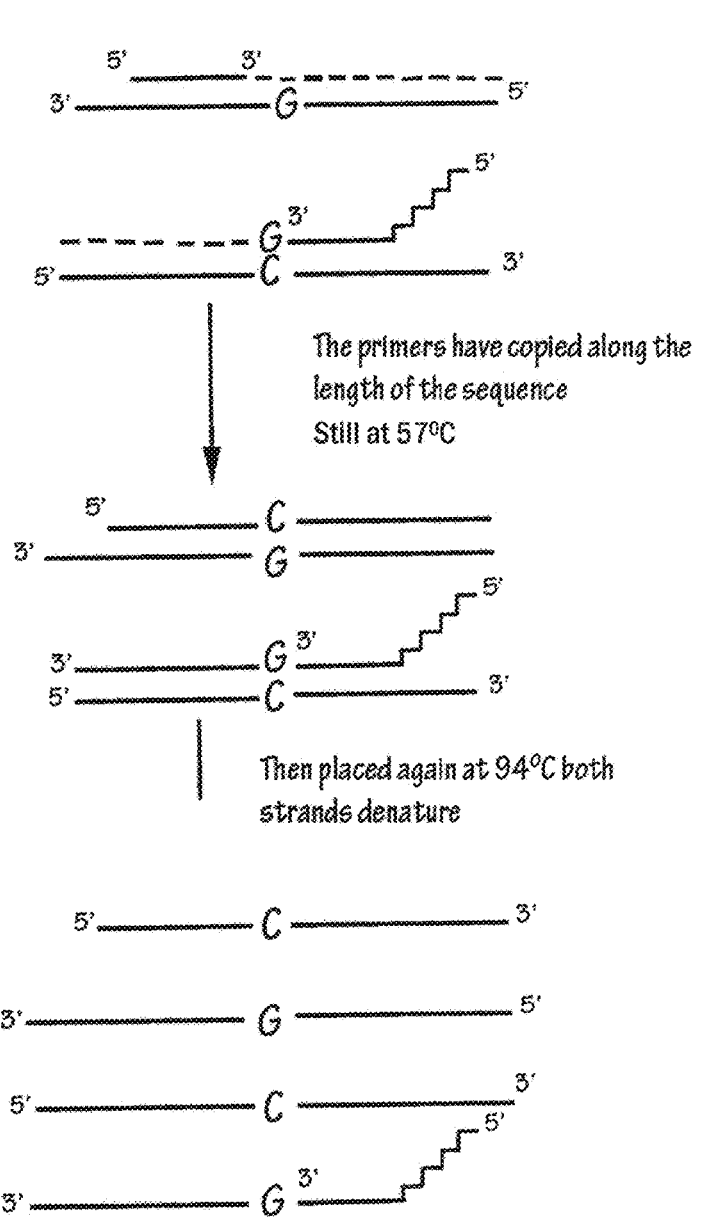
Figure 1J:
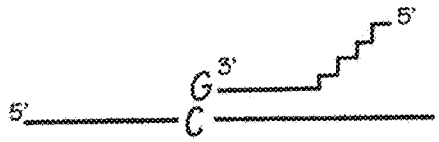
Figure 1J:
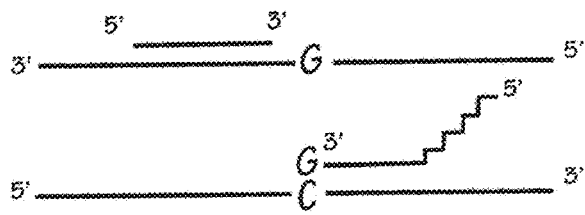
Figure 1J:
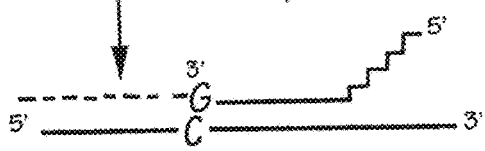
Figure 1J:
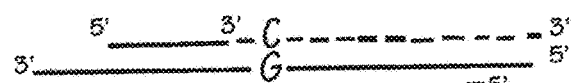
Figure 1J:
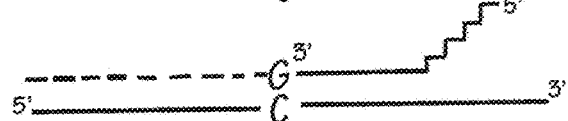
Figure 1J:
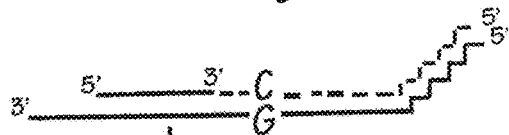
Figure 1K:
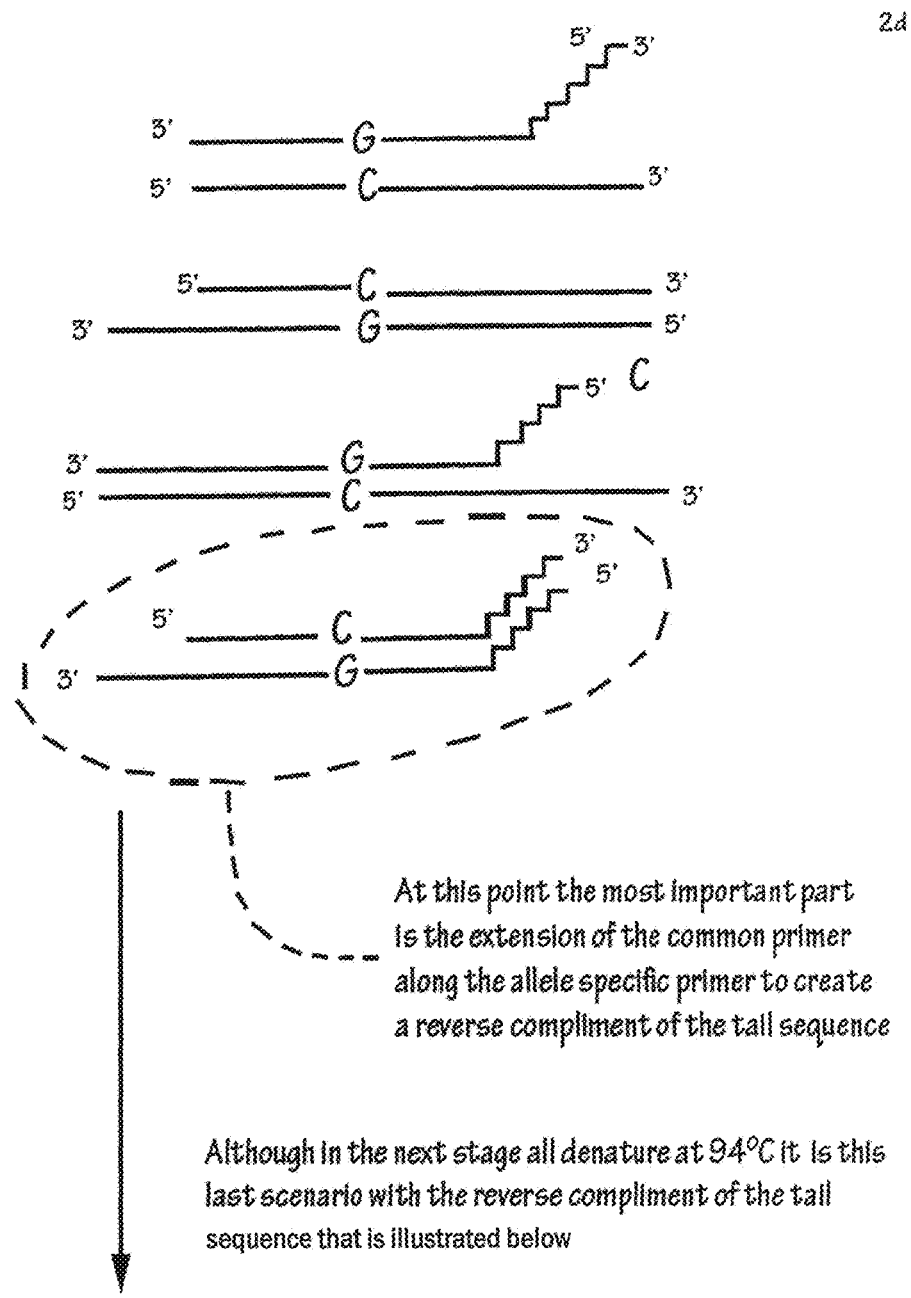
Figure 1L:
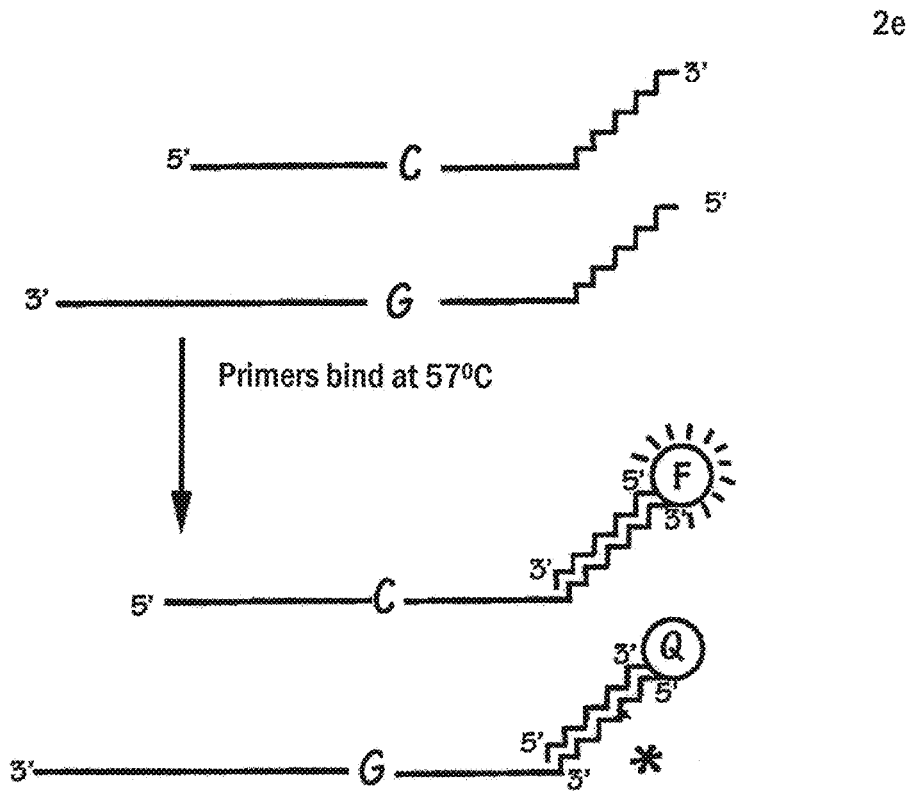

A first aspect of the invention provides a method for the detection of a primer extension product, the method comprising the steps of:
a) providing one or more oligonucleotide primer groups, each group comprising one or more oligonucleotide primer sets, each set characterised by
i) a first oligonucleotide primer (forward primer) having a target-specific portion and a 5' upstream fluorescence cassette-specific portion, and
ii) a second oligonucleotide primer (reverse primer) having a target specific portion
wherein the oligonucleotide primers in a particular set are suitable respectively for hybridisation on complementary strands of a corresponding target nucleotide sequence to permit formation of a primer extension product, for example a PCR product
and wherein the first oligonucleotide primer of each set in the same group contains a fluorescence cassette-specific portion that is capable of hybridising to the complement of the fluorescence cassette-specific portion of the first oligonucleotide primer of any set in the same group
b) providing one or more cassette oligonucleotide sets, each set characterised by
i) a first cassette oligonucleotide labelled with a fluorescent moiety (donor moiety) and having a sequence that is capable of hybridisation to the complement of the fluorescence cassette-specific portion of the first oligonucleotide primer of any set in a given oligonucleotide primer group; and
ii) a second cassette oligonucleotide labelled with an acceptor moiety (for example a quencher moiety)
wherein each set of cassette oligonucleotides hybridises to one another to form a fluorescent quenched pair, wherein the fluorescent quenched pair has a Tm A,
c) initiating the primer extension reaction thereby generating (if the relevant target polynucleotide is present) a complementary sequence to the relevant first oligonucleotide primer,
such that the relevant second (acceptor, for example quencher, labelled) cassette oligonucleotide is less able to hybridise to the relevant first (fluorescently labelled) cassette oligonucleotide, whereby a signal is generated; and
d) detecting the signal that is generated,
wherein the primer extension reaction is performed at least in part at a Ta that is less than the Tm A or Tm As for the one or more fluorescent quenched pairs.

The signal may be measured in real-time. Alternatively the signal may be measured at the end point of the reaction.

The or a first cassette oligonucleotide labelled with a fluorescent moiety may be capable of acting as a primer in a primer extension reaction (for example may have a 3' OH group). Alternatively, the or a first cassette oligonucleotide labelled with a fluorescent moiety may not capable of acting as a primer in the primer extension reaction (or it may not matter whether or not it is capable of acting as a primer). It is considered that generally more primer extension product is formed, and hence a better signal obtained, if the or a first cassette oligonucleotide labelled with a fluorescent moiety is capable of acting as a primer in the primer extension reaction. The acceptor/quencher labelled fluorescence cassette oligonucleotide may typically not be capable of acting as a primer in a primer extension reaction, for example because the acceptor/quencher may prevent the oligonucleotide from acting as a primer.

The Tm of an oligonucleotide is the temperature in ° C. at which 50% of the molecules in a population of a single-stranded oligonucleotide are hybridised to their complementary sequence and 50% of the molecules in the population are not-hybridised to said complementary sequence. The Tm of the fluorescent quenched pair (for example) may be measured empirically, for example Tm may be measured using melting curve analysis, e.g. using a Roche LightCycler 480 instrument on a 96-well white plate. The Tm may preferably be measured using the same instrumentation as that used to conduct the primer extension reaction. The Tm of the fluorescent quenched pairs (cassettes) may be tested in standard reaction buffer in the absence of polymerase. Standard reaction buffer is indicated in the Examples. Further representative details are also provided in the examples. Melting peaks may be generated from melt curve data by the LightCycler 480 analysis function (–dF/dt). Tms are calculated by using a manual Tm option to identify the lowest point in the inverse melt peak.

Where reference is made to a Tm for hybridisation involving part of an oligonucleotide, the relevant Tm is considered to be the Tm that can be determined for a hybridisation using a test oligonucleotide corresponding to the relevant part of the first oligonucleotide.

The Tm (Tm A) of the fluorescent quenched pair or pairs is preferably less than or equal to 15° C., e.g. less than or equal to 10° C., above the Ta of the primer extension reaction, for example between 1 and 15° C., such as between 1 and 10° C., above the Ta of the primer extension reaction. The Tm A or Tm As should be selected to be high enough to prevent non-specific detection while low enough not to inhibit detection (considered to be by inhibiting the primer extension reaction). The term Ta will be well known to those skilled in the art and refers to the temperature (typically set or programmed into the apparatus controlling the reaction parameters) at which significant amplification occurs during the primer extension reaction. Typically the same Ta will be used substantially throughout a primer extension reaction. Sometimes a different Ta (typically higher) will be used in initial rounds of a primer extension reaction. The Tm of the fluorescent quenched pair (or pairs, if multiple fluorescent quenched pairs are being used) is typically above any Ta used during the course of a primer extension reaction, or above the Ta used for the preponderance of cycles of the primer extension reaction, for example is less than or equal to 15° C., e.g. less than or equal to 10° C., above the highest or preponderant Ta of the primer extension reaction, for example between 1 and 15° C., such as between 1 and 10° C., above the highest or preponderant Ta of the primer extension reaction. Typically the Ta may be between around 46 and 65° C., for example between 50 and 60° C.

In the present invention, one or both of the pair of labelled fluorescent cassette oligonucleotides (or the primer oligonucleotides) may contain modified bases such as phosphorothioate-modified bases. The number of phosphodiester linkages replaced by phosphorothioates in any given oligonucleotide/primer can range from none to all of the phosphodiester bonds being replaced by phosphothioates, for example one, two, three, four or more. The oligonucleotide(s)/primer(s) may contain phosphorothioates at the 5' and/or 3' termini, however it is preferred that, as an alternative to or addition to such terminal modifications, at least one of the internal bases of the oligonucleotide/primer is a phosphorothioate. For example 10-90%, 20-80%, 30-70% or 40-60% of the bases may be phosphorothioates. In one embodiment the phosphorothioate-modified bases (where there is more than one) are separated by at least one, e.g. one to three, unmodified (phosphorodiester) bases, for example alternate bases within the oligonucleotide(s)/primer(s) may be phosphorothioates. In an example, it may be particularly useful for the fluorescent (donor) labelled fluorescent cassette oligonucleotide or oligonucleotides to contain phosphorothioate-modified bases. It is considered that the presence of phosphorothioate-modified bases may assist in reducing the formation of aberrant products that may be fluorescent and therefore lead to generation of erroneous fluorescence signal. See, for example, PCT/GB2012/050645, for discussion of phosphorothioate incorporation patterns that are considered also to be useful in relation to the present invention.

The signal that is generated in the methods of the invention may be detected by measuring the signal at any point during or after the primer extension reaction. Measurement of the signal may be qualitative or quantitative. It is not considered necessary to have to adapt the temperature of the reaction specifically in order to be able to measure the signal. The signal can be detected during the normal course of the primer extension reaction.

The present invention finds use in a variety of different applications, and is particularly suited for use in PCR based reactions, and for applications including SNP detection applications, allelic variation detection applications, gene expression studies, copy number variation studies, real-time and end point PCR, and the like.

As indicated above, the present invention finds utility in template-dependent primer extension reactions and for determining the production of primer extension products in a primer extension reaction mixture, e.g. detecting whether primer extension products are produced in a primer extension reaction. By primer extension product is meant a nucleic acid molecule that results from a template-dependent primer extension reaction. Template-dependent primer extension reactions are those reactions in which a polymerase extends a nucleic acid primer molecule that is hybridised to a template nucleic acid molecule, where the sequence of bases that is added to the terminus of the primer nucleic acid molecule is determined by the sequence of bases in the template strand. Template-dependent primer extension reactions include both amplification and non-amplification primer extension reactions. In some embodiments of the subject invention, the template-dependent primer extension reaction in which the production of primer extension products is detected is an amplification reaction, e.g. a polymerase chain reaction (PCR).

Nucleic acid targets which may be identified using the methods of the invention include any nucleic acid-containing targets, such as native DNA or RNA. The nucleic acids may where appropriate include sequences that include any of the known base analogs of DNA and RNA such as 4 acetylcytosine, 8-hydroxy-N6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethyl-am inomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxy-amino-methyl-2-thiouracil, beta-D- mannosylqueosine, 5'-methoxycarbonylmethyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine and 2,6-diaminopurine; or they may contain PNAs.

The oligonucleotides used in the method of the invention may include such base analogs or PNAs as appropriate, though this may not be typical.

In practicing the methods of the invention, the first step is to produce a primer extension mixture, e.g. a composition that includes all of the elements necessary for a primer extension reaction to occur. In an example the primer extension mixture typically includes at least one pair of labelled oligonucleotides (the cassette oligonucleotide set or sets) for use in a primer extension reaction which oligonucleotides hybridise to one another to form a fluorescent quenched pair, wherein one oligonucleotide is labelled with a fluorescent moiety and the other oligonucleotide is labelled with a quenching moiety, wherein the fluorescent quenched pair has a Tm (Tm A) which is above the Ta of the primer extension reaction. The fluorescent labelled oligonucleotide of each set comprises a sequence that is capable of hybridisation to the complement(s) of the 5' upstream fluorescence cassette-specific region of the first oligonucleotide primer (forward primer) of each primer set of a particular group. The forward primers in a group each have a (typically different) target-specific portion and a (typically identical or closely related) 5' upstream fluorescence cassette-specific portion. Upon introduction (for example by the progress of the primer extension reaction when the target nucleic acid to which the primers of a particular primer set are directed is present) of a complementary sequence to the 5' upstream fluorescence cassette-specific portion (to which the fluorescent labelled fluorescence cassette oligonucleotide is able to hybridise), a detectable signal is generated, because the acceptor (quencher) labelled fluorescence cassette oligonucleotide is less able to bind to and quench the signal from) the fluorescent (donor) labelled fluorescence cassette oligonucleotide. As the primer extension reaction progresses and more of the extension product to which the fluorescent labelled fluorescence cassette oligonucleotide is able to hybridise is generated, generally the greater the signal produced.

Thus, in addition to the fluorophore domain, the fluorescent labelled oligonucleotide also comprises a sequence that is capable of hybridisation to the complement of the 5' upstream tail portion or portions (fluorescence cassette-specific portion or portions) of a given group of first oligonucleotide primers (forward primers), This "tag" sequence binds to a nucleic acid sequence (extension product) which is created as a complement to the tagged primer or primers included in the reaction (which may be unlabelled, or which may e.g. in subsequent rounds of the primer extension reaction, be the fluorescent labelled cassette oligonucleotide itself), e.g. under stringent hybridisation conditions, for example in the primer extension reaction mixture at a temperature at or above the Ta, for example with a Tm that is at least the Ta.

As noted above, the fluorescence cassette-specific portion or "tag" sequence of each of the first oligonucleotide primers (forward primers) in a particular group may typically be identical or closely related, for example be the same length or differ in length by less than about 10, more typically 5, 4, 3, 2 or 1 nucleotides and have at least about 80, 85, 90, more typically at least about 95, 96, 97, 98, 99 or 100% identity with each other in the region of overlap. For example, there may be no more than 3, 2 or 1 non-identical nucleotides. It may be most straightforward for these fluorescence cassette-specific portions to be identical, but it is not essential, which allows more flexibility in oligonucleotide design.

The fluorescence cassette-specific portion or tag sequence or sequences of one group typically will differ significantly from those of a different group, so that there is no practically relevant hybridisation between the fluorescence cassette-specific portion(s) of one group and the complements of the fluorescence cassette-specific portion(s) of another group, as will be apparent to those skilled in the art.

In addition to the acceptor domain, the acceptor moiety labelled cassette oligonucleotide is capable of hybridising to the corresponding fluorescent labelled cassette oligonucleotide to form a fluorescent quenched pair, wherein the fluorescent quenched pair has a Tm A.

Typically the fluorescent labelled cassette oligonucleotide does not comprise a target sequence specific portion i.e. does not comprise a sequence hybridising (at the Ta of the primer extension reaction) to the target polynucleotide that the target specific portion of the first oligonucleotide primer or primers is intended to hybridise with. Thus, in such an arrangement, the fluorescent labelled cassette oligonucleotide is not tied to a particular target sequence but may be used (with appropriate oligonucleotide primer sets) in the detection of a primer extension product, arising from any target sequence. The fluorescent labelled cassette oligonucleotide (and corresponding acceptor/quencher labelled cassette oligonucleotide) may be included in a "master" assay mix, to be used alongside an (target specific) "assay" mix. Typically, the acceptor/donor labelled cassette oligonucleotide does not comprise target sequence specific portion either.

Typically the fluorescent labelled cassette oligonucleotide consists of the fluorescent moiety (donor moiety) and the sequence that is capable of hybridisation to the complement of the fluorescence cassette-specific portion of a first oligonucleotide primer. Typically the acceptor/quencher labelled cassette oligonucleotide consists of the acceptor/quencher moiety and the sequence that is capable of hybridisation to the fluoresecence cassette-specific portion of the fluorescent labelled cassette oligonucleotide.

It may be desirable for the interaction between the fluorescent (donor) labelled fluorescence cassette oligonucleotide and the acceptor (quencher) labelled fluorescence cassette oligonucleotide to be less stable than the interaction between the fluorescent (donor) labelled fluorescence cassette oligonucleotide and the extension product complementary to the 5' upstream fluorescence cassette-specific portion of the forward oligonucleotide primer of each primer set of the relevant group. Such an arrangement may be useful in achieving an optimal balance between avoiding generation of aberrant signal and allowing the primer extension reaction to proceed efficiently. Thus, the Tm for the hybridisation between the fluorescent (donor) labelled fluorescence cassette oligonucleotide and the acceptor (quencher) labelled fluorescence cassette oligonucleotide may be lower than the Tm Tm C (or Tms; Tm Cs) for the hybridisation between the fluorescent (donor) labelled fluorescence cassette oligonucleotide and the extension product complementary to the 5' upstream fluorescence cassette-specific portion of the forward oligonucleotide primer of each primer set of the relevant group. Thus, the Ta of the primer extension reaction is lower than the Tm A or Tm As for the fluorescent quenched pair or pairs, which may in turn be lower (for example between about 1 and 10° C. lower) than the Tm C or Tm Cs (ie for the hybridisation between the fluorescently labelled oligonucleotide(s) and the primer extension product(s) being formed).

Note that there may (but need not) be a different Tm C for each primer set, so there may be multiple Tm Cs relevant to each group (of primer sets) as well as multiple Tm Cs relevant to different groups. Typically the Tm Cs relevant to a particular group (of primer sets) are higher than the Tm A for the relevant fluorescence cassette set. Typically all Tm As in a particular primer extension reaction are higher than the Ta for that reaction. Typically all the Tm Cs for a particular primer extension reaction will be within around 10, more typically 5, 4, 3, 2 or 1° C. of each other, Typically all the Tm As for a particular primer extension reaction will be within around 10, more typically 5, 4, 3, 2 or 1° C. of each other.

In an example (for example when the fluorescent labelled cassette oligonucleotide does not comprise a target-specific sequence), the quencher labelled cassette oligonucleotide is between 1 and 5 nucleotide bases shorter than the fluorescent labelled cassette oligonucleotide, Typically the unpaired (relative to the quencher labelled cassette oligonucleotide) portion of the fluorescent labelled cassette oligonucleotide is at the 3' end of the fluorescent labelled cassette oligonucleotide or "opposite" the 5' end of the quencher labelled cassette oligonucleotide. The portion of the relevant oligonucleotide primer (or primers) whose complement hybridises to the fluorescent labelled cassette oligonucleotide typically is within about 5 nucleotides of the length (for example between 5, 4, 3, 2, or 1 nucleotides shorter and 5, 4, 3, 2, or 1 nucleotides longer; for example the same length) of the fluorescence labelled cassette oligonucleotide, for example with any difference in length typically at the 5' end of the oligonucleotide primer and fluorescence labelled cassette oligonucleotide. In subsequent rounds of the primer extension reaction, the fluorescent labelled cassette oligonucleotide itself can act as the primer, so the complement formed during primer extension will generally extend to the 5' end of the fluorescent labelled cassette oligonucleotide. Thus, the portion of the complement that hybridises to the quencher labelled cassette oligonucleotide is typically as long as the quencher labelled cassette oligonucleotide.

In other examples, there may alternatively or in addition be more (or more significant) mismatches between the quencher labelled cassette oligonucleotide and the fluorescent labelled cassette oligonucleotide than between the complement to the relevant oligonucleotide primer (or primers) and the fluorescent labelled cassette oligonucleotide. As is well known to those skilled in the art, the position of a mismatch within an oligonucleotide pair and the nature of the mismatch (for example whether an A:T pairing is disrupted or a G:C pairing) will influence the significance of the mismatch on the change in stability/change in Tm.

In yet further examples, alternatively or in addition different nucleotides/bases may be used in the quencher labelled cassette oligonucleotide relative to those used in the primer extension reaction mix (and hence incorporated into the complement to the primers) thereby altering the relative stability of the hybridisations between the quencher labelled cassette oligonucleotide and the fluorescent labelled cassette oligonucleotide and primer extension product. Typically the "non-standard" base or bases may be used in the quencher labelled cassette oligonucletide, and "standard" bases in the primer extension mix, but other arrangements are also possible, as will be apparent to the skilled person.

It will be appreciated that if, in a different arrangement, the fluorescent labelled cassette oligonucleotide comprises not only a "tag" sequence but also a sequence complementary to the target nucleic acid to be detected (see "direct" embodiment described later), that there will be a considerably longer region of complementarity between the fluorescent labelled cassette oligonucleotide and the extension product than if the fluorescent labelled cassette oligonucleotide has a "tag" sequence but no sequence complementary to the target nucleic acid to be detected. It is considered that in this arrangement there is less advantage to be derived from the Tm A for the fluorescent quenched pair being reduced, Thus, it is not considered to provide particular benefit for, for example, the region corresponding to the "tag" in the acceptor labelled cassette oligonucleotide to be shorter or to have mismatches or different base composition compared to the "tag" in the fluorophore labelled cassette oligonucleotide. It is noted that this arrangement (termed "direct" arrangement below) is considered to be potentially useful, but means that at least a different fluorescent/donor labelled oligonucleotide is typically needed for each target sequence to be detected, whereas in the previous ("indirect") arrangement in which there is no target-specific sequence (e.g. able to hybridise at the Ta of the primer extension reaction) it is not necessary to synthesise a different fluorescent/donor labelled oligonucleotide (or acceptor/quencher labelled oligonucleotide) for each target sequence (of which there may be many hundreds or thousands of possibilities) to be detected. In a given primer extension reaction, a different fluorescent/donor labelled oligonucleotide is typically needed for each target sequence (for example 2, 3, 4, or 5, as discussed further below) being analysed in that particular primer extension reaction, but the same collection of fluorescence cassette oligonucleotides can potentially be used with any target sequences.

Depending on the nature of the oligonucleotide and the assay itself (for example whether the "direct" or "indirect" arrangement is used), at least the "tag" region of the fluorescent labelled cassette oligonucleotide may hybridise to a region of the primer extension product. For example, where the assay is a SNP genotyping assay, e.g. in which a universal ("indirect") cassette reporting system is employed, the tag region hybridises under stringent conditions to the tag region of primer extension product.

As noted above, in examples the hybridising region in the acceptor moiety labelled cassette oligonucleotide may be shorter (for example 1 to 5 nucleotides shorter) than the sequence in the fluorophore labelled cassette oligonucleotide that hybridises to the extension product, or may have a mismatch, or a different type of base, so that the Tm A for hybridisation between the cassette oligonucleotides is less than the Tm C (or Tm Cs) for hybridisation between the fluorescent labelled cassette oligonucleotide and the extension product (or extension products).

Fluorescent energy transfer occurs when a suitable fluorescent energy donor and an energy acceptor moiety are in close proximity to one another. The excitation energy absorbed by the donor is transferred to the acceptor which can then further dissipate this energy either by fluorescent emission if a fluorophore, or by non-fluorescent means if a quencher. A donor-acceptor pair comprises two—a fluorescence group and a fluorescence-modifying group having overlapping spectra, where the donor (fluorescence group) emission overlaps the acceptor (fluorescence-modifying) absorption, so that there is energy transfer from the excited fluorophore to the other member of the pair. As such, the labelled oligonucleotides pair(s) (fluorescence cassette oligonucleotide sets) of the invention are nucleic acid detectors that include on separate oligonucleotides a fluorophore domain where the fluorescent energy donor, i.e. donor, is positioned and a second oligonucelotide with an acceptor domain where the fluorescent energy acceptor, i.e. acceptor, is positioned. As mentioned above, the donor oligonucleotide includes the donor fluorophore. The donor fluorophore may be positioned anywhere in the nucleic acid detector, but is typically present at the 5' end of the oligonucleotide.

The acceptor domain includes the fluorescence energy acceptor. The acceptor may be positioned anywhere in the acceptor domain, but is typically present at the 3' end of the oligonucleotide.

In the present invention, in a pair of labelled oligonucleotides each of the cassette oligonucleotides may contain one or more labels, for example 1, 2 or 3 labels. One or both of the cassette oligonucleotides preferably contains a single label, more preferably both of the oligonucleotides contain a single label.

For example the fluorescent labelled cassette oligonucleotide preferably contains a label at or within the 5' end of the oligonucleotide and the quencher labelled cassette oligonucleotide contains a label at or within the 3' end of the oligonucleotide.

The fluorophores for the labelled oligonucleotide pairs may be selected so as to be from a similar chemical family or a different one, such as cyanine dyes, xanthenes or the like. Fluorophores of interest include, but are not limited to fluorescein dyes (e.g. 5-carboxyfluorescein (5-FAM), 6-carboxyfluorescein (6-FAM), 2',4',1,4,-tetrachlorofluorescein (TET), 2',4',5',7',1,4-hexachlorofluorescein (HEX), and 2',7'-dimethoxy-4',5'-dichloro-6-carboxyfluorescein (JOE)), cyanine dyes such as Cy5, dansyl derivatives, rhodamine dyes (e.g. tetramethyl-6-carboxyrhodamine (TAM RA), and tetrapropano-6-carboxyrhodamine (ROX)), DABCYL, DABCYL, cyanine, such as Cy3, anthraquinone, nitrothiazole, and nitroimidazole compounds, or other non-intercalating dyes. Fluorophores of interest are further described in International Patent Applications WO 01/42505 and WO 01/86001.

If more than one primer groups are used (for example 1, 2, 3, 4, 5, 6, 7, 8, 9, or 10) and consequently several cassette oligonucleotide sets, the fluorophore group may typically be different for each of the 1, 2, 3, 4, 5, 6, 7, 8, 9 or 10 (or more) cassette oligonucleotide sets. The acceptor (for example quencher) group may be the same or different so long as they are able to modulate the fluorescence of the paired fluorophore group in satisfactory fashion. Typically 1, 2, 3, or 4 different primer groups (each of which may have one or more primer sets, typically one primer set) and consequently 1, 2, 3 or 4 cassette oligonucleotide sets may be used in a single reaction tube. A limiting factor may be the number of different spectra that it is possible to distinguish, which may depend on the characteristics of the fluorescence generating/measuring equipment available. Considerations in choosing compatible sets of fluorophores and acceptors/quenchers will be known to those skilled in the art.

In the methods of the invention the polymerase employed in the primer extension reaction includes at least one Family A, where the terms "Family A" and "Family B" correspond to the classification scheme reported in Braithwaite & Ito, Nucleic Acids Res. (1993) 21:787-802. Family A polymerases of interest include: *Thermus aquaticus* polymerases, including the naturally occurring polymerase (Taq) and derivatives and homologues thereof, such as Klentaq (as described in Proc. Natl. Acad. Sci USA (1994) 91:2216-2220); *Thermus thermophilus* polymerases, including the naturally occurring polymerase (Tth) and derivatives and homologues thereof, and the like. The polymerase for use in the invention may be used in purified or unpurified form. Typically the polymerase lacks exonuclease activity. This may give better specificity, for example in an SNP typing assay, as will be apparent to those skilled in the art, Another component of the reaction mixture produced in the first step of the methods is the template nucleic acid. The nucleic acid that serves as template may be single stranded or double stranded, where the nucleic acid is typically deoxyribonucleic acid (DNA). The length of the template nucleic acid may be as short as 20 bp, but usually be at least about 50 or 100 bp long, and more usually at least about 150 bp long, and may be as long as 1,000 or 10,000 bp or longer, e.g. 50,000 bp in length or longer, including a genomic DNA extract, digest thereof or crude lysate, etc. The nucleic acid may be free in solution, flanked at one or both ends with non-template nucleic acid, present in a vector, e.g. plasmid and the like, with the only criteria being that the nucleic acid be available for participation in the primer extension reaction. The template nucleic acid may be present in purified form, or in a complex mixture with other non-template nucleic acids, e.g. in cellular DNA preparation, etc.

The template nucleic acid may be derived from a variety of different sources, depending on the application for which the PCR is being performed, where such sources include organisms that comprise nucleic acids, i.e. viruses; prokaryotes, e.g. bacteria, archaea and cyanobacteria; and eukaryotes, e.g. members of the kingdom protista, such as flagellates, amoebas and their relatives, amoeboid parasites, ciliates and the like; members of the kingdom fungi, such as slime molds, acellular slime molds, cellular slime molds, water molds, true molds, conjugating fungi, sac fungi, club fungi, imperfect fungi and the like; plants, such as algae, mosses, liverworts, hornworts, club mosses, horsetails, ferns, gymnosperms and flowering plants, both monocots and dicots; and animals, including sponges, members of the phylum cnidaria, e.g. jelly fish, corals and the like, combjellies, worms, rotifers, roundworms, annelids, molluscs, arthropods, echinoderms, acorn worms, and vertebrates, including reptiles, fishes, birds, snakes, and mammals, e.g. rodents, primates, including humans. The template nucleic acid may be used directly from its naturally occurring source, e.g. as a crude lysate and/or it may preprocessed in a number of different ways, as is known in the art. In some embodiments, the template nucleic acid may be from a synthetic source.

A component of the reaction mixture produced in the first step of the subject methods is the primers employed in the primer extension reaction, e.g. the PCR primers (such as forward and reverse primers employed in geometric amplification). As already indicated, one or more oligonucleotide primer groups may be used, each group comprising one or more oligonucleotide primer sets. Each set may typically have a forwards and a reverse primer. As noted above, typically 1, 2, 3, 4 or more primer groups may be used. Each group may typically include one primer set (unless, for example, there is a reason why it is wished to measure the combined amplification products arising from two separate sets of primers). Each primer extension reaction mix typically will comprise at least one forward primer and usually two or three forward primers and more usually five or seven forward primers in the case of a SNP genotyping reaction. A corresponding reverse primer for each forward primer may also be present, but these may not be different, for example in a SNP genotyping reaction, where a common reverse primer may be used with several different forward primers.

A primer extension reaction mix will comprise at least a fluorescently-labelled (donor) primer and a complementary acceptor, quencher labelled oligonucleotide (which typically is not capable of acting as a primer, for example because the quencher is positioned at the 3' end and prevents the oligonucleotide from being able to act as a primer).

More usually, for example in the case of exponential amplification, the primer extension mix may typically comprise at least a fluorescent/donor labelled primer and a complementary acceptor/quencher labelled oligonucleotide, and a reverse unlabelled primer, where one of or any of the oligonucleotides or primers may contain at least one modified, e.g. phosphorothioate, group. Most usually, in the case of exponential amplification using a universal reporter system, the primer extension mix will comprise at least a fluorescently acceptor labelled primer and a complementary donor, quencher labelled oligonucleotide, a reverse unlabelled primer and an unlabelled tagged forward primer. The primers may be at least 15 bp in length, e.g. at least 20 bp or 22 bp in length. Primers may be 30 bp in length or longer, for example, the length of the primers may be 18 to 60 bp in length, such as from about 20 to 35 bp in length. The tagged primer will typically be longer than the fluorescent cassette oligonucleotides (as it typically will need to contain a tag sequence long enough to hybridise to its complement at the Ta of the primer extension reaction; as well as a target sequence specific portion that also has to be long enough to hybridise to its complement at the Ta of the primer extension reaction) or the (typically untagged) reverse primer.

It may be desirable for there to be an excess in the primer extension reaction (and hence in the reaction mix before initiation of the primer extension reaction) of acceptor labelled cassette oligonucleotide relative to fluorophore labelled cassette oligonucleotide. A ratio of at least 1:1, 1.5:1, 2:1, 3:1, 4:1 or 5:1, for example between 1:1 and 10:1 or 15:1, for example between 1.5:1 and 5:1 acceptor-labelled to fluorophore-labelled cassette oligonucleotide in a cassette oligonucleotide set may be useful in optimising the signal achieved and/or minimising the signal arising in a "no template control" (NTC).

As used herein, "nucleic acid" means either DNA, RNA, single-stranded or double-stranded, and any chemical modifications thereof. Modifications include, but are not limited to, those which provide other chemical groups that incorporate additional charge, polarisability, hydrogen bonding, electrostatic interaction, and functionality to the nucleic acid. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping.

As used herein, "complementary" refers to the pair of nitrogenous bases, consisting of a purine linked by hydrogen bonds to a pyrimidine, that connects the complementary strands of DNA or of hybrid molecules joining DNA and RNA.

As used herein, "fluorescent group" refers to a molecule that, when excited with light having a selected wavelength, emits light of a different wavelength. Fluorescent groups may also be referred to as "fluorophores".

As used herein, "fluorescence-modifying group" refers to a molecule that can alter in any way the fluorescence emission from a fluorescent group. A fluorescence-modifying group generally accomplishes this through an energy transfer mechanism. Depending on the identity of the fluorescence-modifying group, the fluorescence emission can undergo a number of alterations, including, but not limited to, attenuation, complete quenching, enhancement, a shift in wavelength, a shift in polarity, a change in fluorescence lifetime. One example of a fluorescence-modifying group is a quenching group.

As used herein, "energy transfer" refers to the process by which the fluorescence emission of a fluorescent group is altered by a fluorescence-modifying group. If the fluorescence-modifying group is a quenching group, then the fluorescence emission from the fluorescent group is attenuated (quenched). Energy transfer can occur through fluorescence resonance energy transfer, or through direct energy transfer. The exact energy transfer mechanisms in these two cases are different. It is to be understood that any reference to energy transfer in the present application encompasses all of these mechanistically-distinct phenomena. Energy transfer is also referred to herein as fluorescent energy transfer or FET.

As used herein, "energy transfer pair" refers to any two molecules that participate in energy transfer. Typically, one of the molecules acts as a fluorescent group, and the other acts as a fluorescence-modifying group. Such pairs may comprise, for example, two fluorescent groups which may be different from one another and one quenching group, two quenching groups and one fluorescent group, or multiple fluorescent groups and multiple quenching groups. In cases where there are multiple fluorescent groups and/or multiple quenching groups, the individual fluorescent and/or quenching groups may be different from one another. The preferred energy transfer pairs of the invention comprise a fluorescent group and a quenching group. In some cases, the distinction between the fluorescent group and the fluorescence-modifying group may be blurred. For example, under certain circumstances, two adjacent fluorescein groups can quench one another's fluorescence emission via direct energy transfer. For this reason, there is no limitation on the identity of the individual members of the energy transfer pair in this application. All that is required is that the spectroscopic properties of the energy transfer pair as a whole change in some measurable way if the distance between the individual members is altered by some critical amount.

As used herein, "primer" refers to an oligonucleotide which is capable of acting as a point of initiation of synthesis when placed under conditions in which synthesis of a primer extension product which is complementary to a nucleic acid strand can occur. Thus, an oligonucleotide capable of acting as a primer may typically have a 3' OH group.

As used herein, "quenching group" refers to any fluorescence-modifying group that can attenuate at least partly the light emitted by a fluorescent group. We refer herein to this attenuation as "quenching". Hence, illumination of the fluorescent group in the presence of the quenching group leads to an emission signal that is less intense than expected, or even completely absent. Quenching occurs through energy transfer between the fluorescent group and the quenching group.

As used herein, "fluorescence resonance energy transfer" or "FRET" refers to an energy transfer phenomenon in which the light emitted by the excited fluorescent group is absorbed at least partially by a fluorescence-modifying group. If the fluorescence-modifying group is a quenching group, then that group can either radiate the absorbed light as light of a different wavelength, or it can dissipate it as heat. FRET depends on an overlap between the emission spectrum of the fluorescent group and the absorption spectrum of the quenching group. FRET also depends on the distance between the quenching group and the fluorescent group. Above a certain critical distance, the quenching group is unable to absorb the light emitted by the fluorescent group, or can do so only poorly.

As used herein "tailed primer" refers to an oligonucleotide containing at least two domains, one specific to the target nucleic acid, e.g. DNA, of interest, i.e. capable of hybridising to said target nucleic acid, and the other sequence (typically 5' of the target-specific sequence), serving as a template for production of extension product comprising the complement of the "tag" sequence. The complement of the "tag" sequence may then bind to, for example, the "tag" portion of the corresponding fluorescent labelled cassette oligonucleotide (which may lack any sequence other than "tag" portion). The tagged primers may also comprise additional regions such as a linker between the two domains referred to above and/or tags.

As used herein "direct energy transfer" refers to an energy transfer mechanism in which passage of a photon between the fluorescent group and the fluorescence-modifying group does not occur. Without being bound by a single mechanism, it is believed that in direct energy transfer, the fluorescent group and the fluorescence-modifying group interfere with each other's electronic structure. If the fluorescence-modifying group is a quenching group, this will result in the quenching group preventing the fluorescent group from emitting light.

In general, quenching by direct energy transfer is more efficient than quenching by FRET. Indeed, some quenching groups that do not quench particular fluorescent groups by FRET (because they do not have the necessary spectral overlap with the fluorescent group) can do so efficiently by direct energy transfer. Furthermore, some fluorescent groups can act as quenching groups themselves if they are close enough to other fluorescent groups to cause direct energy transfer. For example, under these conditions, two adjacent fluorescein groups can quench one another's fluorescence effectively. For these reasons, there is no limitation on the nature of the fluorescent groups and quenching groups useful for the practice of this invention.

Where reference is made to "hybridisation" or the ability of an oligonucleotide and/or primer to "hybridise" to another nucleotide sequence, the skilled person will understand that such hybridisation is capable of occurring under the conditions prevalent in the template-extension reaction, e.g. PCR reaction, in which the oligonucleotide and/or primer is utilised.

The invention also provides a kit suitable for use in a method for the detection of a primer extension product, the method comprising the steps of:
a) two or more oligonucleotide primer groups, each group comprising one or more oligonucleotide primer sets, each set characterised by
i) a first oligonucleotide primer (forward primer) having a target-specific portion and a 5' upstream fluorescence cassette-specific portion, and
ii) a second oligonucleotide primer (reverse primer) having a target specific portion
wherein the oligonucleotide primers in a particular set are suitable respectively for hybridisation on complementary strands of a corresponding target nucleotide sequence to permit formation of a primer extension product, for example a PCR product
and wherein the first oligonucleotide primer of each set in the same group contains a fluorescence cassette-specific portion that is capable of hybridising to the complement of the fluorescence cassette-specific portion of the first oligonucleotide primer of any set in the same group; and
b) two or more cassette oligonucleotide sets, each set characterised by
i) a first cassette oligonucleotide labelled with a fluorescent moiety (donor moiety) and having a sequence that is capable of hybridisation to the complement of the fluorescence cassette-specific portion of the first oligonucleotide primer of any set in a given oligonucleotide primer group; and
ii) a second cassette oligonucleotide labelled with an acceptor moiety (for example a quencher moiety)
wherein each set of cassette oligonucleotides hybridises to one another to form a fluorescent quenched pair, wherein the fluorescent quenched pair has a Tm A,
wherein each of the Tm As for the fluorescent quenched pairs is above a temperature suitable for use as the Ta of a primer extension reaction using the oligonucleotides of the kit, for example above a temperature between 46 and 65° C., for example between 50 and 60° C.

The first oligonucleotide primers may typically be unlabelled. The fluorescent labelled cassette oligonucleotide typically does not comprise a target-specific sequence. The Tm A for the hybridisation between the fluorescent (donor) labelled fluorescence cassette oligonucleotide and the acceptor (quencher) labelled fluorescence cassette oligonucleotide may be lower than the Tm Tm C (or Tms; Tm Cs) for the hybridisation between the fluorescent (donor) labelled fluorescence cassette oligonucleotide and the extension product complementary to the 5' upstream fluorescence cassette-specific portion of the forward oligonucleotide primer of each primer set of the relevant group. The quencher labelled cassette oligonucleotide may be between 1 and 5 nucleotide bases shorter than the fluorescent labelled cassette oligonucleotide, Further preferences for the oligonucleotides and primer extension reaction are as indicated above.

The kits according to the invention may also contain a polymerase and/or other components suitable for use in primer extension reactions such as divalent cations, e.g. derived from magnesium salts, deoxyribonucleotide 5' triphosphates (dNTPs), buffering agents, etc.

The kit may comprise the one or more cassette oligonucleotide sets in a first container, optionally wherein the first container comprises other components for performing a primer extension reaction, such as buffer, thermostable DNA polymerase, and optionally wherein the first cassette oligonucleotides do not comprise a target-specific portion; and one or more oligonucleotide primer groups in a separate further container or containers.

A further aspect of the invention provides a method for the detection of a primer extension product, the method comprising the steps of:
a) providing one or more oligonucleotide primer groups, each group comprising one or more oligonucleotide primer sets, each set characterised by
i) a first labelled oligonucleotide primer (forward primer) having a target-specific portion and a 5' upstream fluorescence cassette-specific portion, and
ii) a second oligonucleotide primer (reverse primer) having a target specific portion
wherein the oligonucleotide primers in a particular set are suitable respectively for hybridisation on complementary strands of a corresponding target nucleotide sequence to permit formation of a primer extension product, for example a PCR product and wherein the first oligonucleotide primer of each set in the same group contains a fluorescence cassette-specific portion that is capable of hybridising to the complement of the fluorescence cassette-specific portion of the first oligonucleotide primer of any set in the same group b) providing one or more cassette oligonucleotide sets, each set characterised by i) a first cassette oligonucleotide or oligonucleotides labelled with a fluorescent moiety (donor moiety) that is the first labelled oligonucleotide primer or primers (forward primer or primers) of a primer group ii) a second cassette oligonucleotide labelled with an acceptor moiety (for example a quencher moiety)

wherein each set of cassette oligonucleotides hybridises to one another to form a fluorescent quenched pair, wherein the fluorescent quenched pair has a Tm A, c) initiating the primer extension reaction thereby generating (if the relevant target polynucleotide is present) a complementary sequence to the relevant first oligonucleotide primer, such that the relevant second (acceptor, for example quencher, labelled) cassette oligonucleotide is less able to hybridise to the relevant first (fluorescently labelled) cassette oligonucleotide, whereby a signal is generated; and d) detecting the signal that is generated, wherein the primer extension reaction is performed at least in part at a Ta that is less than the Tm A or Tm As for the one or more fluorescent quenched pairs.

This may be determined a "direct" detection method.

The methods or kits of the invention are considered to be useful in a variety of circumstances, for example for use in allele specific PCR based SNP Genotyping, gene expression studies or copy number variation studies.

Examples of the use of the present invention include the following:

Direct (Real-Time) Detection of PCR Products:

This embodiment utilises a fluorescently-labelled tailed oligonucleotide primer to initiate the PCR process and generate the fluorescence. Thus, the first oligonucleotide primer and the corresponding first cassette oligonucleotide labelled with a fluorescent moiety are typically the same entity. This primer is directed to the template (target polynucleotide) region of interest and therefore drives the specificity of the reaction. A complementary quencher labelled oligonucleotide of the invention is also used. As the length of the quencher labelled oligonucleotide is long enough to give a Tm above the Ta of the reaction the product generation can be assessed at each cycle of the PCR process on any real-time PCR instrument (such as a ABI 7900 Prism instrument) or at the end of the reaction.

Due to the complementarity of the two labelled oligonucleotides (quencher and fluorescently labelled tailed primer), they hybridise to each other. This hybridisation brings the quencher label in very close proximity to the fluorophore, thereby rendering all fluorescent signal from the fluorophore quenched, when excited at a suitable wavelength, e.g. 488 nm when the fluorophore in FAM.

Also included in the reaction is a conventional reverse primer to create a PCR primer pair. The PCR process is then initiated and PCR product begins to be generated.

During PCR amplification and the formation of PCR, the complementary sequence to the fluorescent primer is generated. This amplified sequence, lacking the quencher, competes with the quencher oligonucleotide to bind with the fluorescently labelled tailed primer. Those fluorescently labelled incorporated tailed primers are no longer quenched but produce a fluorescent signal which is directly proportional to the amount of PCR product generated.

Indirect (Real-Time) Detection of PCR Products

This embodiment utilises a conventional (unlabelled) oligonucleotide (primer) to initiate the PCR process. This conventional primer is tailed with a DNA sequence that is not directed to the amplicon region of interest. This tag sequence is positioned at the 5' portion of the primer. Also included in the reaction is a single fluorescently-labelled oligonucleotide that is capable of hybridising to the complement of the tag sequence region of the conventional primer generated in the reaction. A number of suitable fluorophores exist, with a popular choice being FAM (a derivative of fluorescein). Finally, included in the reaction is a 3' quencher-labelled oligonucleotide antisense to the FAM labelled oligonucleotide. A number of suitable labels exist of which the Black Hole quencher series of labels are a popular choice.

As the length of the quencher oligonucleotide is long enough to give a Tm above the Ta of the reaction the product generation can be assessed at each cycle of the PCR process on any real-time PCR instrument (such as a Roche LC480 or ABI 7900 Prism instrument).

Due to the complementarity of the two labelled oligonucleotides, they hybridise to each other. This hybridisation brings the quencher label in very close proximity to the fluorophore, thereby rendering all fluorescent signal from the fluorophore quenched. The PCR process is then initiated and PCR product begins to be generated. After the first few cycles of PCR the complementary sequence to the fluorescent primer is generated. The fluorescent PCR primer is then able to initiate synthesis during the PCR, and does so. It is not essential that the fluorescent oligonucleotide is able to act as a primer, but it is considered that more PCR product may be generated if the fluorescent oligonucleotide acts as a primer, which may provide a better signal. This produces an amplicon containing a fluorescent molecule. Once this occurs the quenching oligo less able to hybridise to the fluorescent labelled oligonucleotide, as the PCR process produces double-stranded amplicon DNA. As the quenching oligonucleotide is no longer hybridised to the fluorescent labelled oligonucleotide, signal is then generated which is directly proportional to the amount of PCR product generated and can be measured on a cycle by cycle basis.

The tag region of the tailed primer need not be identical to the single fluorescently-labelled oligonucleotide, as long as a complementary sequence of the tail region generated hybridises to the fluorescently-labelled oligonucleotide.

Indirect (end-point) Detection of PCR Products—SNP Genotyping:

This embodiment, illustrated in FIG. 1, utilises the same fluorophore- and quencher-labelled oligonucleotide pair(s) as described above.

SNP genotyping utilises at least two labelled oligonucleotide pairs, for example 2, 3 or 4 pairs, wherein each pair preferably comprises a different fluorophore, which fluorophores are spectrally-resolvable from each other, e.g. FAM and HEX. The tailed primers (each corresponding to a different oligonucleotide primer group, as indicated above) are tailed with a distinct sequence, the non-tailed portion of the primers (generally termed forward) are directed to the DNA of interest. In this portion of the primer they may differ from one another only by a single nucleotide e.g. at their 3' terminal base. Each primer is directed to the polymorphic base in the DNA of interest, as well known to those skilled in the art. PCR is conducted whereby the primers only initiate synthesis when they match the target sequence of interest, e.g. when the 3' base is perfectly matched. When a mismatch occurs synthesis does not proceed.

During the reaction, the non-tail (target specific) portion depending on the genotype is able to initiate synthesis (or both are, in the case of a heterozygote). This results in incorporation of the distinct fluorescent tail portion of the primer in to the PCR product thereby hindering the hybridisation of the quencher oligonucleotide to the corresponding fluorescent oligonucleotide. Signal is therefore generated according to which of the allele-specific oligonucleotides has initiated the synthesis. The amplification products incorporating one or more of the fluorophores may then be read on a fluorescent plate-reader. The resulting data may then be plotted and a cluster plot of one fluorophore over the other is generated. The resulting genotypes are then able to be determined based on the cluster plots.

In this specification and the appended claims, the singular forms "a", "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the ranges, and are also encompassed within the invention, subject to any specifically excluded limit in the stated range. Where the stated range includes one or both of the limits, ranges excluding either or both of those included limits are also included in the invention.

All publications mentioned herein are incorporated herein by reference to the fullest extent possible for the purpose of describing and disclosing those components that are described in the publications which might be used in connection with the presently described invention.

The invention will now be described by reference to the following examples which are for illustrative purposes and are not to be construed as a limitation of the scope of the present invention.

EXAMPLES

Abbreviations

6FAM: 6-Carboxy Fluorescein
HEX: 2',4',5',7',1,4-Hexachlorofluorescein
Dab: Non-fluorescent dark quencher
*: Incorporation of phosphorothioate (Phosphorothioates (or S-oligos) are a variant of normal DNA in which one of the nonbridging oxygens is replaced by sulphur).
$T_m$: Oligonucleotide Melting temperature
$T_a$: annealing temperature of an amplification reaction A series of five fluor/quencher cassettes were used to demonstrate the effect of cassette melting temperature on the control of non-specific amplification. The sequences of these fluor/quencher cassettes are detailed below.

Cassette Pair 1:

[SEQ ID NO: 1]
FAM fluorescent oligonucleotide:
/6FAM/TGA GCG ATT AGC CGT TAG GAT GA

[SEQ ID NO: 2]
FAM complementary quenching oligonucleotide:
AAC CTA ACG GCT AAT CGC TCA/Dab/

[SEQ ID NO: 3]
HEX fluorescent oligonucleotide:
/HEX/GCT GGT CGG TGA ACA GGT TAG AGA

[SEQ ID NO: 4]
HEX complementary quenching oligonucleotide:
TAA CCT GTT CAC CGA CCA GC/Dab/

Cassette Pair 2:

[SEQ ID NO: 5]
FAM fluorescent oligonucleotide:
/6FAM/TCA GTG AGC GAT TAG CCG TTA GGA TGA

[SEQ ID NO: 6]
FAM complementary quenching oligonucleotide:
AAC CTA ACG GCT AAT CGC TCA CTG A/Dab

[SEQ ID NO: 7]
HEX fluorescent oligonucleotide:
/HEX/TAC AGC TGG TCG GTG AAC AGG TTA GAG A

[SEQ ID NO: 8]
HEX complementary quenching oligonucleotide:
TAA CCT GTT CAC CGA CCA GCT GTA/Dab/

Cassette Pair 3:

[SEQ ID NO: 9]
FAM fluorescent oligonucleotide:
/6FAM/TGT CTC AGT GAG CGA TTA GCC GTT AGG ATG A

[SEQ ID NO: 10]
FAM complementary quenching oligonucleotide:
AAC CTA ACG GCT AAT CGC TCA CTG AGA CA/Dab

[SEQ ID NO: 11]
HEX fluorescent oligonucleotide:
/5HEX/ATG CTA CAG CTG GTC GGT GAA CAG GTT AGA GA

[SEQ ID NO: 12]
HEX complementary quenching oligonucleotide:
TAA CCT GTT CAC CGA CCA GCT GTA GCA T/Dab/

Cassette Pair 4:

[SEQ ID NO: 13]
FAM fluorescent oligonucleotide:
/6FAM/ATG CTG TCT CAG TGA GCG ATT AGC CGT TAG GAT GA

[SEQ ID NO: 14]
FAM complementary quenching oligonucleotide:
AAC CTA ACG GCT AAT CGC TCA CTG AGA CAG CAT/Dab/

[SEQ ID NO: 15]
HEX fluorescent oligonucleotide:
/5HEX/AAG CAT GCT ACA GCT GGT CGG TGA ACA GGT TAG AGA

[SEQ ID NO: 16]
HEX complementary quenching oligonucleotide:
TAA CCT GTT CAC CGA CCA GCT GTA GCA TGC TT/Dab/

Cassette Pair 5:

FAM fluorescent oligonucleotide: [SEQ ID NO: 17]
/6FAM/G*CG*AT*TA*GC*CG*TT*AG*GA*TG*A FAM complementary quenching oligonucleotide: [SEQ ID NO: 18]
CCTAACGGCTAATCGC/Dab/

HEX fluorescent oligonucleotide: [SEQ ID NO: 19]
/5HEX/G*TC*GG*TG*AA*CA*GG*TT*AG*AG*A HEX complementary quenching oligonucleotide: [SEQ ID NO: 20]
5'AACCTGTTCACCGAC/Dab/

The incorporation of phosphorothioate into the fluor/quencher cassette is described in patent application PCT/GB2012/050645. A number of variants on Cassette 5 could also be used instead of those listed. A selection of the sequence variants that could be used to replace those listed are:

1) /6FAM/GCGATTAGCCGTTAGGATGA [SEQ ID NO: 17]

2) /6FAM/GCGATTAGCCGTTAGGATG*A [SEQ ID NO: 17]

3) /6FAM/G*C*G*A*T*T*A*G*C*C*G*T*T*AG*G*A*T*G*A [SEQ ID NO: 17]

4) /HEX/GTCGGTGAACAGGTTAGAGA [SEQ ID NO: 19]

5) /HEX/GTCGGTGAACAGGTTAGAG*A [SEQ ID NO: 19]

6) /5HEX/*G*T*C*G*T*G*A*A*C*A*G*G*T*T*A*G*A*G*A [SEQ ID NO: 19]

7) C*CT*AA*CG*GC*TA*AT*CG*C/3Dab/ [SEQ ID NO: 18]

8) CC*TA*AC*GG*CT*AA*TC*GC/3Dab/ [SEQ ID NO: 18]

9) C*C*T*A*A*C*G*G*C*T*A*A*T*C*G*C/3Dab/ [SEQ ID NO: 18]

10) AA*CC*TG*TT*CA*CC*GA*/3Dab/ [SEQ ID NO: 27]

11) A*AC*CT*GT*TC*AC*CG*AC/3Dab/ [SEQ ID NO: 20]

12) A*A*C*C*T*G*T*T*C*A*C*C*G*A*C/3Dab/ [SEQ ID NO: 20]

Example 1: Determination of the Melting Temperature of Fluor/Quencher Cassettes

Melting temperatures of the fluor/quencher cassettes were determined experimentally. Cassettes 1 to 5 were incorporated into a reaction mix containing the following components at final concentration:
1) 0.1 uM FAM-labelled oligonucleotide
2) 0.1 uM HEX-labelled oligonucleotide
3) 0.5 uM Quencher-labelled oligonucleotide (antisense to FAM-labelled oligonucleotide)
4) 0.5 uM Quencher-labelled oligonucleotide (antisense to HEX-labelled oligonucleotide)
5) 8.5 mM Tris/HCl pH 8.3
6) 42.5 mM KCl
7) 1.8 mM Magnesium chloride
8) 165.2 uM dNTPs
9) 212.5 nM 5-carboxy-X-rhodamine, SE (5-ROX, SE)
10) 0.04% Igepal Melting temperatures for each cassette were determined in the absence of DNA polymerase. Melting curve analysis of each fluor/quencher cassette was carried out on a Roche LightCycler 480 instrument on a 96-well white plate using 10 ul of the reaction mix per well.

Melting curve analysis was preceded by heating of the mix to 95° C. for 30 seconds. Melting curve analysis was carried out from 40 to 95 degrees at 0.06° C./sec. Six replicates were tested for each cassette. Melting peaks were generated from melt curve data by the LightCycler 480 analysis function (−dF/dt). $T_m$s were calculated by using the manual $T_m$ option to identify the lowest point in the inverse melt peak (this is necessary since automatic $T_m$ calculation is not possible in inverted peaks using this software). Experimentally-determined $T_m$s for each fluor/quencher cassette are listed below:

FAM-labelled fluorescent oligonucleotides and corresponding quenchers:

|  | 1 | 2 | 3 | 4 | 5 |
|---|---|---|---|---|---|
| Mean | 63.22 | 67.42 | 70.33 | 73.20 | 55.81 |
| Minimum | 63.13 | 67.27 | 70.31 | 73.07 | 55.68 |
| Maximum | 63.27 | 67.55 | 70.45 | 73.41 | 55.95 |

HEX-labelled fluorescent oligonucleotides and corresponding quenchers:

|  | 1 | 2 | 3 | 4 | 5 |
|---|---|---|---|---|---|
| Mean | 68.65 | 69.95 | 72.57 | 74.88 | 56.60 |
| Minimum | 68.50 | 69.81 | 72.44 | 74.72 | 56.53 |
| Maximum | 68.91 | 70.09 | 72.72 | 74.93 | 56.80 |

Example 2—Endpoint Detection of Fluorescence 1

A direct comparison was carried out between Cassette 1 and Cassette 5. Cassette 1 has an experimentally-determined $T_m$ above the annealing temperature used for this amplification reaction. Cassette 5 has an experimentally-determined $T_m$ below the annealing temperature of the amplification reaction (see Example 1).

All oligonucleotides were purchased freeze-dried and were resuspended to 200 μM initial concentrations in 10 mM Tris/HCl pH 8.0. All further dilutions were carried out in this diluent.

Amplification was carried out in 4 μl reaction volumes in 384-well black plates. A 1× reaction mix contained the following components:
1) 0.16 uM Allele-specific primer 1
2) 0.16 uM Allele-specific primer 2
3) 0.41 uM Reverse (common) primer
4) 0.1 uM FAM-labelled oligonucleotide
5) 0.1 uM HEX-labelled oligonucleotide
6) 0.5 uM Quencher-labelled oligonucleotide (antisense to FAM-labelled oligonucleotide)
7) 0.5 uM Quencher-labelled oligonucleotide (antisense to HEX-labelled oligonucleotide)
8) 8.5 mM Tris/HCl pH 8.3

9) 42.5 mM KCl
10) 1.8 mM Magnesium chloride
11) 165.2 uM dNTPs
12) 212.5 nM 5-carboxy-X-rhodamine, SE (5-ROX, SE)
13) 0.04% Igepal In addition to the components listed each mix should contain 2-50 μl/ml N-terminal truncated polymerase enzyme without exonuclease activity. It is not essential that the enzyme is without exonuclease activity but is preferable, particularly for SNP analysis.

Assay-specific primers used were:

```
                                             [SEQ ID NO: 21]
Allele specific primer 1:
5'GCGATTAGCCGTTAGGATGATGAAGCTCCACAATTTGGTGAATTATCA
AT3'

[SEQ ID NO: 22]
Allele specific primer 2:
5'GTCGGTGAACAGGTTAGAGATGAAGCTCCACAATTTGGTGAATTATCA
AA3'

[SEQ ID NO: 23]
Common reverse primer:
5'CACTCTAGTACTATATCTGTCACATGGTA3'
```

The use of phosphorothioate additions to oligonucleotides is described in patent application PCT/GB2012/050645. Phosphorothioate-labelled assay primers can also be used. Examples of alternative primers that could be substituted for those listed above are:

```
                                             [SEQ ID NO: 21]
1)   5'GCGATTAGCCGTTAGGATGATGAAGCTCCACAATTTGGTGAAT
     TATCAA*T3'

[SEQ ID NO: 22]
2)   5'GTCGGTGAACAGGTTAGAGATGAAGCTCCACAATTTGGTGAAT
     TATCAA*A3'

[SEQ ID NO: 21]
3)   5'G*CG*AT*TA*GC*CG*TT*AG*GA*TG*AT*GA*AG*CT*CC*
     AC*AA*TT*TG*GT*GA*AT*TA*TC*AA*T3'

[SEQ ID NO: 22]
4)   5'G*TC*GG*TG*AA*CA*GG*TT*AG*AG*AT*GA*AG*CT*CC*
     AC*AA*TT*TG*GT*GA*AT*TA*TC*AA*A3'

[SEQ ID NO: 23]
5)   5'CA*CT*CT*AG*TA*CT*AT*AT*CT*GT*CA*CA*TG*GT*A3'

[SEQ ID NO: 21]
6)   5'G*C*G*A*T*T*A*G*C*C*G*T*T*A*G*G*A*T*G*A*A*T*
     G*A*A*G*C*T*C*C*A*C*A*A*T*T*T*G*G*T*G*A*A*T*T*
     A*T*C*A*A*T3'

[SEQ ID NO: 22]
7)   5'G*T*C*G*G*T*G*A*A*C*A*G*G*T*T*A*G*A*G*A*T*G*
     A*A*G*C*T*C*C*A*C*A*A*T*T*T*G*G*T*G*A*A*T*T*A*
     T*C*A*A*A3'

[SEQ ID NO: 23]
8)   5'C*A*C*T*C*T*A*G*T*A*C*T*A*T*A*T*C*T*G*T*C*A*
     C*A*T*G*G*T*A3'
```

Amplification reactions were carried out on a water bath based Hydrocycler PCR machine. Amplification conditions were:
94° C. for 15 minutes (hot-start activation)
60 cycles of:
94° C. for 20 seconds
57° C. for 60 seconds (ie a Ta of 57° C.)

Endpoint fluorescence was read at room temperature on BMG Pherastar fluorescent plate reader after the completion of the reaction.

Figure 2:
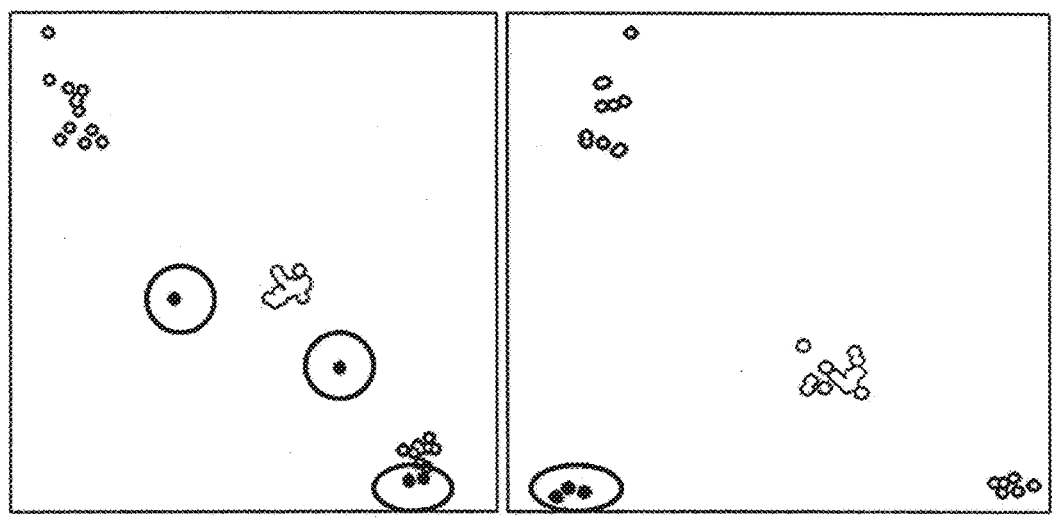
FIG. 2 shows data generated using the assay described in Example 2 below. Example genotyping data for amplification products of fluor/quencher Cassette 5 (left) and fluor/quencher Cassette 1 (right). The three clusters present in each example represent the three possible genotypes that can be detected. No Template Controls are represented in solid black and circled for clarity.

FIG. 2 provides example data from each of the three alleles that can be generated using the primer pair described above. The figure also shows the positions of no template control (NTC) samples (circled) relative to those of each of the three genotype clusters. In the example shown, NTCs from the reaction where the $T_m$ is below the $T_a$ of the amplification reaction (left) are clearly distinct from one another and provide evidence of non-specific amplification. Example data for Cassette 1 (right), for which the $T_m$ is above the $T_a$ of the amplification reaction, shows that the NTCs in this reaction remain tightly clustered, with a fluorescence below that of the appropriate amplified sample cluster. This indicates that no non-specific products have been generated.

Example 3—Endpoint Detection of Fluorescence 2

A direct comparison was carried out between Cassette 1 and Cassette 5. Cassette 1 has an experimentally-determined $T_m$ above the annealing temperature used for this amplification reaction. Cassette 5 has an experimentally-determined $T_m$ below the annealing temperature of the amplification reaction (see Example 1).

All oligonucleotides were purchased freeze-dried and were resuspended to 200 μM initial concentrations in 10 mM Tris/HCl pH 8.0. All further dilutions were carried out in this diluent.

Amplification was carried out in 4 μl reaction volumes in 384-well black plates. A 1× reaction mix contained the following components:

1) 0.16 uM Allele-specific primer 1
2) 0.16 uM Allele-specific primer 2
3) 0.41 uM Reverse (common) primer
4) 0.1 uM FAM-labelled oligonucleotide
5) 0.1 uM HEX-labelled oligonucleotide
6) 0.5 uM Quencher-labelled oligonucleotide (antisense to FAM-labelled oligonucleotide)
7) 0.5 uM Quencher-labelled oligonucleotide (antisense to HEX-labelled oligonucleotide)
8) 10 mM Tris/HCl pH 8.3
9) 10 mM KCl
10) 1.8 mM Magnesium chloride
11) 165.2 uM dNTPs
12) 212.5 nM 5-carboxy-X-rhodamine, SE (5-ROX, SE)

In addition to the components listed each mix should contain 2-50 μl/ml N-terminal truncated polymerase enzyme without exonuclease activity.

```
                                             [SEQ ID NO: 24]
Allele specific primer 1:
5' GCGATTAGCCGTTAGGATGATCATTCTCATAATCGCCCACGGA 3'

[SEQ ID NO: 25]
Allele specific primer 2:
5'GTCGGTGAACAGGTTAGAGATCATTCTCATAATCGCCCACGGG 3'

[SEQ ID NO: 26]
Common reverse primer:
5' GTAGTTTGAGTTTGCTAGGCAGAATAGTA 3'
```

Amplification reactions were carried out on a Hydrocycler PCR machine. Amplification conditions were:
94° C. for 15 minutes (hot-start activation)
10 cycles of:
94° C. for 20 seconds
61° C.-55° C. Touch Down for 60 seconds (0.6° C. per cycle)
35 cycles of:
94° C. for 20 seconds
55° C. for 60 seconds Endpoint fluorescence was read at room temperature on a BMG Pherastar fluorescent plate reader after the completion of the reaction.

Figure 3:
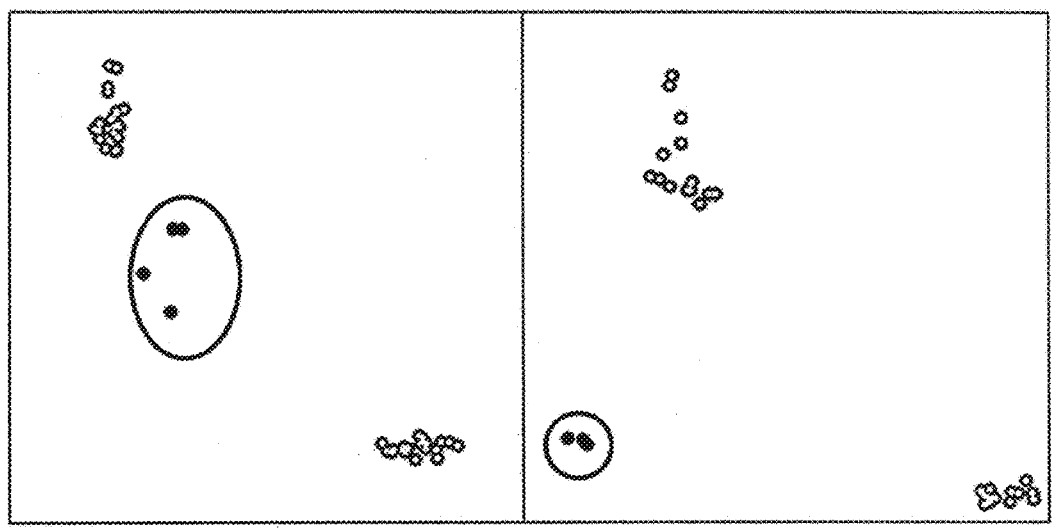
FIG. 3 shows data generated using the assay described in Example 3 below. Example genotyping data for amplification products of fluor/quencher Cassette 5 (left) and fluor/quencher Cassette 1 (right). The two clusters present in each example represent the two possible genotypes that can be detected. No Template Controls are represented in solid black and circled for clarity.

FIG. 3 provides example data from each of the two alleles that can be generated using the primer pair described above. The figure also shows the positions of no template control (NTC) samples (circled) relative to those of each of the two genotype clusters. In the example shown, NTCs from the reaction where the $T_m$ is below the $T_a$ of the amplification reaction (left) have a FAM fluorescence substantially higher than that of products amplified using the HEX primer and a HEX fluorescence substantially higher than that of products amplified using the FAM primer. This data provides evidence of non-specific amplification. Example data for Cassette 1 (right), for which the $T_m$ is above the $T_a$ of the amplification reaction, shows that the NTCs in this reaction remain tightly clustered towards the bottom left-hand corner of the figure. This indicates that little or no non-specific products have been generated.

Example 4—Real-Time Detection of Fluorescence

Amplification reactions were carried out in conjunction with real-time fluorescence detection in order to demonstrate the effect of increasing the melt temperature of the fluor/quencher cassette.

All oligonucleotides were purchased freeze-dried and were resuspended to 200 μM initial concentrations in 10 mM Tris/HCl pH 8.0. All further dilutions were carried out in this diluent. Real-time amplification was carried out in 10 μl reaction volumes in 96-well white plates. A 1× reaction mix contained the following components:
14) 0.16 uM Allele-specific primer 1
15) 0.16 uM Allele-specific primer 2
16) 0.41 uM Reverse (common) primer
17) 0.1 uM FAM-labelled oligonucleotide
18) 0.1 uM HEX-labelled oligonucleotide
19) 0.5 uM Quencher-labelled oligonucleotide (antisense to FAM-labelled oligonucleotide)
20) 0.5 uM Quencher-labelled oligonucleotide (antisense to HEX-labelled oligonucleotide)
21) 8.5 mM Tris/HCl pH 8.3
22) 42.5 mM KCl
23) 1.8 mM Magnesium chloride
24) 165.2 uM dNTPs
25) 212.5 nM 5-carboxy-X-rhodamine, SE (5-ROX, SE)
26) 0.04% Igepal In addition to the components listed each mix should contain 2-50 μl/ml N-terminal truncated polymerase enzyme without exonuclease activity.

Assay-specific primers used were:

```
                                                     [SEQ ID NO: 21]
Allele specific primer 1:
5'GCGATTAGCCGTTAGGATGATGAAGCTCCACAATTTGGTGAATTATCA
AT3'

[SEQ ID NO: 22]
Allele specific primer 2:
5'GTCGGTGAACAGGTTAGAGATGAAGCTCCACAATTTGGTGAATTATCA
AA3'

[SEQ ID NO: 23]
Common reverse primer:
5'CACTCTAGTACTATATCTGTCACATGGTA3'
```

Real-time applications of the described mix were tested in 96-well white plates on the Roche LightCycler 480 real-time PCR instrument. 5 μl of the 2× assay mix was added to 5 μl human genomic DNA previously diluted to a concentration of 3-4 ng/μl. The plate was sealed using LC480 QPCR seal. The plate was thermally-cycled in an LC480 real-time PCR machine (Roche) under the following cycling conditions; change in FAM and HEX fluorescence was recorded in real-time at every cycle.
94° C. for 15 minutes (hot-start activation)
60 cycles of:
94° C. for 10 seconds
57° C. for 60 seconds (plate read at this temperature)

Figure 4:
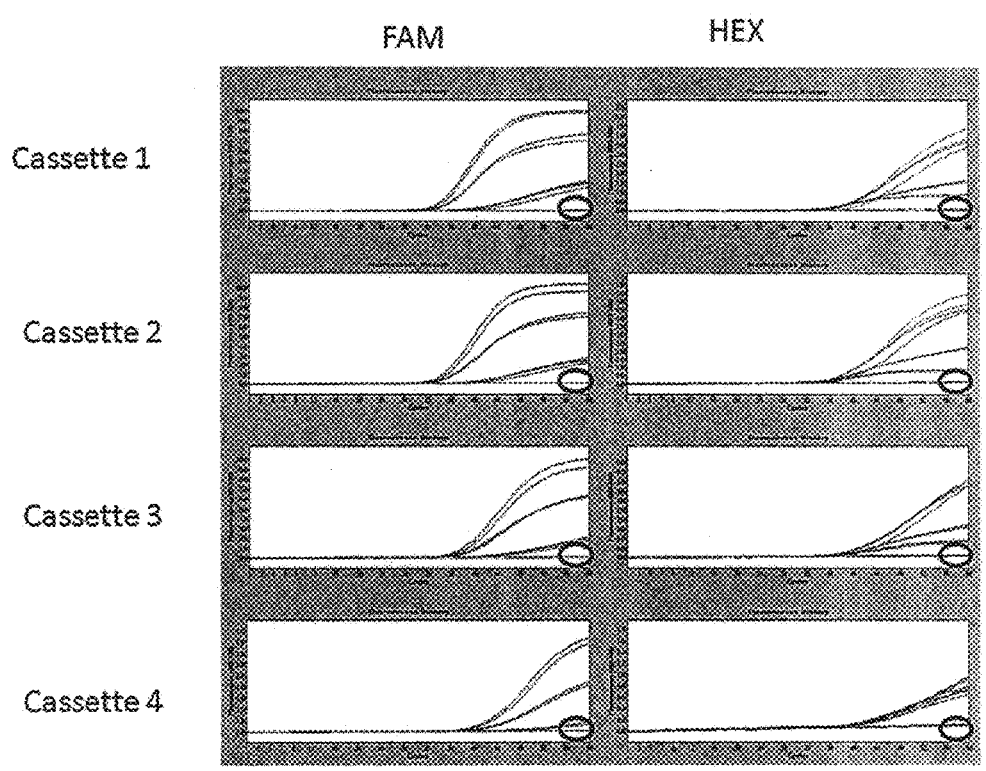
FIG. 4 shows data generated using the assay described in Example 4 below. Example genotyping data for amplification products of fluor/quencher Cassettes 1 to 4. In all cases allele-specific amplification is demonstrated in the absence of No Template Control detection. No Template Controls are represented in solid black and circled for clarity.

The PCR was run for 60 cycles to demonstrate the efficiency of higher $T_m$ fluor/quencher cassette on reduction of NTC amplification. Real-time detection results are shown in FIG. 4. No Template Control results are circled. Real-time detection of non-specific NTC product does not occur in real-time since the $T_m$ of the fluor-quencher cassettes is above the $T_a$ of the amplification reaction.

The invention claimed is:

1. A method for the detection of a primer extension product, the method comprising the steps of:
   a) providing one or more oligonucleotide primer groups, each group comprising one or more oligonucleotide primer sets, each set comprising
      i) a first oligonucleotide primer having a target-specific portion and a 5' upstream fluorescence cassette-specific portion, and
      ii) a second oligonucleotide primer having a target specific portion,
      wherein the oligonucleotide primers in a particular set are suitable respectively for hybridisation on complementary strands of a corresponding target nucleotide sequence to permit formation of a primer extension product,
      and wherein the first oligonucleotide primer of each set in the same group contains a fluorescence cassette-specific portion that is capable of hybridising to the complement of the fluorescence cassette-specific portion of the first oligonucleotide primer of any set in the same group;
   b) providing one or more fluorescence cassette oligonucleotide sets, each set comprising
      i) a first cassette oligonucleotide labelled with a fluorescent moiety that is a donor moiety and having a sequence that is capable of hybridisation to the complement of the fluorescence cassette-specific portion of the first oligonucleotide primer of any set in a given oligonucleotide primer group, and not comprising a target specific sequence portion; and
      ii) a second cassette oligonucleotide labelled with an acceptor moiety wherein the second cassette oligonucleotide does not comprise a target specific sequence and wherein the second cassette oligonucleotide is between 1 and 5 nucleotide bases shorter than the corresponding first cassette oligonucleotide,
      wherein each set of cassette oligonucleotides hybridises to one another to form a fluorescent quenched pair, wherein the fluorescent quenched pair has a Tm A;
   c) initiating the primer extension reaction thereby generating a complementary sequence to the first oligonucleotide primer when the target polynucleotide is present, such that the second cassette oligonucleotide is less able to hybridise to the first cassette oligonucleotide, whereby a signal is generated; and
   d) detecting the signal that is generated;
   wherein the primer extension reaction is performed at least in part at a Ta that is less than the Tm A or Tm As for the one or more fluorescent quenched pairs.

2. The method of claim 1 wherein the Tm A of the fluorescent quenched pair or pairs is less than or equal to 15° C., optionally between 1 and 15° C.; or less than or equal to 10° C., optionally between 1 and 10° C. above the Ta of the primer extension reaction.

3. A method according to claim 1, wherein the signal is measured in real-time.

4. A method according to claim 1, wherein the signal is measured at the end point of the reaction.

5. The method of claim 1, wherein the first cassette oligonucleotide labelled with a fluorescent moiety is capable of acting as a primer in a primer extension reaction.

6. The method of claim 1, wherein the first cassette oligonucleotide labelled with a fluorescent moiety is not capable of acting as a primer in the primer extension reaction.

7. The method of claim 1, wherein the interaction between the fluorescent donor labelled fluorescence cassette oligonucleotide and the acceptor labelled fluorescence cassette oligonucleotide is less stable than the interaction between the fluorescent donor labelled fluorescence cassette oligonucleotide and the extension product complementary to the 5' upstream fluorescence cassette-specific portion of the first oligonucleotide primer of each primer set of the group.

8. The method of claim 1, wherein each oligonucleotide primer group comprises one oligonucleotide primer set.

9. The method of claim 1, wherein there are 1, 2, 3, 4, 5, 6, 7, 8, 9 or 10 oligonucleotide primer groups and corresponding cassette oligonucleotide sets.

10. The method of claim 1, wherein one or both of the cassette oligonucleotides contains a single label.

11. The method of claim 10 wherein both of the cassette oligonucleotides contain a single label.

12. The method according to claim 1, wherein the fluorescent labelled cassette oligonucleotide contains a label at or within the 5' end of the oligonucleotide.

13. The method according to claim 1, wherein the quencher labelled cassette oligonucleotide contains a label at or within the 3' end of the oligonucleotide.

14. The method according to claim 1, wherein at least one of the bases of at least one of the oligonucleotides is a phosphorothioate modified base.

15. The method according to claim 14 wherein 20-80% of the bases of at least one of the oligonucleotides are phosphorothioate modified bases.

16. A kit suitable for use in a method for the detection of a primer extension product, comprising:
   a) two or more oligonucleotide primer groups, each group comprising one or more oligonucleotide primer sets, each set comprising i) a first oligonucleotide primer having a target-specific portion and a 5' upstream fluorescence cassette-specific portion, and ii) a second oligonucleotide primer having a target specific portion, wherein the oligonucleotide primers in a particular set are suitable respectively for hybridisation on complementary strands of a corresponding target nucleotide sequence to permit formation of a primer extension product, and wherein the first oligonucleotide primer of each set in the same group contains a fluorescence cassette-specific portion that is capable of hybridising to the complement of the fluorescence cassette-specific portion of the first oligonucleotide primer of any set in the same group; and b) two or more fluorescence cassette oligonucleotide sets, each set comprising i) a first cassette oligonucleotide labelled with a fluorescent moiety that is a donor moiety and having a sequence that is capable of hybridisation to the complement of the fluorescence cassette-specific portion of the first oligonucleotide primer of any set in a given oligonucleotide primer group, and not comprising a target specific sequence portion; and ii) a second cassette oligonucleotide labelled with an acceptor moiety wherein the second cassette oligonucleotide does not comprise a target specific sequence and wherein the second cassette oligonucleotide is between 1 and 5 nucleotide bases shorter than the corresponding first cassette oligonucleotide, wherein each set of cassette oligonucleotides hybridises to one another to form a fluorescent quenched pair, wherein the fluorescent quenched pair has a Tm A, wherein each of the Tm As for the fluorescent quenched pairs is above a temperature suitable for use as the Ta of a primer extension reaction using the oligonucleotides of the kit.

* * * * *